(12) United States Patent
Nishihama et al.

(10) Patent No.: US 8,753,686 B2
(45) Date of Patent: Jun. 17, 2014

(54) SURFACE-TREATING AGENTS, SURFACE-TREATED POWDERS, AND COSMETICS COMPRISING THE SAME

(75) Inventors: Shuji Nishihama, Yokohama (JP); Isamu Kaneda, Yokohoma (JP); Atsushi Sogabe, Yokohoma (JP); Tomo Osawa, Yokohoma (JP); Shin-ichi Yusa, Himeji (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 17 days.

(21) Appl. No.: 13/113,188

(22) Filed: May 23, 2011

(65) Prior Publication Data

US 2011/0280946 A1 Nov. 17, 2011

Related U.S. Application Data

(63) Continuation of application No. 11/576,705, filed as application No. PCT/JP2005/018521 on Oct. 6, 2005, now abandoned.

(30) Foreign Application Priority Data

Oct. 7, 2004 (JP) ................................. 2004-294618
Oct. 7, 2004 (JP) ................................. 2004-294619

(51) Int. Cl.
*A61K 9/16* (2006.01)
*A61K 8/81* (2006.01)
*C08F 22/38* (2006.01)

(52) U.S. Cl.
USPC .................... 424/497; 424/70.16; 526/304

(58) Field of Classification Search
None
See application file for complete search history.

(56) References Cited

U.S. PATENT DOCUMENTS

| | | | |
|---|---|---|---|
| 2,874,151 A | 2/1959 | Medalia et al. | |
| 4,137,392 A | 1/1979 | Gross | |
| 5,350,801 A | 9/1994 | Famili et al. | |
| 5,376,386 A * | 12/1994 | Ganderton et al. | 424/499 |
| 5,760,153 A | 6/1998 | Epple et al. | |
| 5,770,346 A | 6/1998 | Iwasa et al. | |
| 5,955,509 A * | 9/1999 | Webber et al. | 514/772.7 |
| 6,491,898 B1 * | 12/2002 | Yamagishi et al. | 424/49 |
| 2002/0177070 A1 | 11/2002 | Kozawa et al. | |
| 2005/0079195 A1 * | 4/2005 | Kataoka et al. | 424/423 |

FOREIGN PATENT DOCUMENTS

| | | |
|---|---|---|
| DE | 4023577 A1 | 1/1992 |
| EP | 0572128 A2 | 12/1993 |
| EP | 0704509 A1 | 4/1996 |
| EP | 0757079 A1 | 2/1997 |
| EP | 1065234 A2 | 1/2001 |
| GB | 2234514 | 2/1991 |
| JP | 09-235211 | 9/1997 |

OTHER PUBLICATIONS

Patent Abstract of Japan: Publication No. 09-235211, published Sep. 9, 1997; Applicant—Shiseido Co Ltd., eleven pages.
European Search Report for corresponding European Patent Application No. 09158705 mailed Aug. 11, 2009, five pages.
International Search Report for PCT/JP2005/018521 mailed Jan. 17, 2006, two pages.
Japanese Patent Abstract Publication No. 2005-326439 published Nov. 24, 2005, one page.
Japanese Patent Abstract Publication No. 08-337514 published Dec. 24, 1996, one page.
Japanese Patent Abstract Publication No. 60-163973 published Aug. 26, 1985, two pages.
Japanese Patent Abstract Publication No. 62-177070 published Aug. 3, 1987, one page.
Supplementary European Search Report for EP05790586 mailed Sep. 25, 2007, two pages.
Yusa et al, Reversible pH-Induced Formation and Disruption of Unimolecular Micelles of an Amphiphilic Polyelectrolyte, Macromolecules 2002, 35, p. 5243-5249.

* cited by examiner

*Primary Examiner* — Blessing M Fubara
*Assistant Examiner* — Jennifer A Berrios
(74) *Attorney, Agent, or Firm* — Rankin, Hill & Clark LLP

(57) ABSTRACT

To provide surface-treating agents that can provide excellent hydrophobicity to powder and can improve its rinsability, to provide surface-treated powders that are treated with the surface-treating agent, and to provide cosmetics that comprise the surface-treated powder. A surface-treating agent consisting of a polymer which comprises a monomer (A) represented by the general formula (1) described below as a constituent monomer.

[Formula 1]

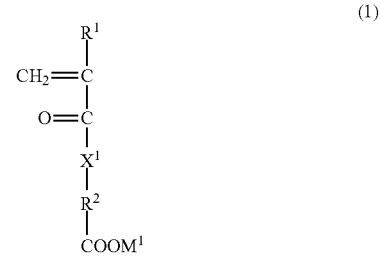

(1)

(wherein $R^1$ represents a hydrogen atom or an alkyl group having 1 to 3 carbon atoms, $R^2$ represents an alkylene group having 4 to 22 carbon atoms, $X^1$ represents an —NH— group or an oxygen atom, and $M^1$ represents a hydrogen atom or a monovalent inorganic or organic cation.)

8 Claims, 5 Drawing Sheets

SURFACE-TREATING AGENTS, SURFACE-TREATED POWDERS, AND COSMETICS COMPRISING THE SAME

RELATED APPLICATIONS

This application claims the priority of Japanese Patent Application No. 2004-294618 filed on Oct. 7, 2004 and Japanese Patent Application No. 2004-294619 filed on Oct. 7, 2004, which are incorporated herein by reference.

BACKGROUND OF THE INVENTION

1. Field of the Invention

The present invention relates to surface-treating agents, surface-treated powders, and cosmetics comprising the same, and in particular, relates to the improvement of hydrophobicity and rinsability of the powder used in cosmetics.

2. Prior Art

For cosmetics, especially for makeup cosmetics, the beautifying effect, which makes people beautiful, is naturally expected. In addition, the sustainability of the beautifying effect, namely, long-lasting makeup is one of very important required characteristics. Thus, in the development of cosmetic base material, one of important themes has been longer-lasting makeup. In the field of makeup cosmetics, oily bases are often used so that the makeup does not deteriorate with moisture such as sweat, tears, and saliva. When hydrophilic powder is blended in an oily base, the powder easily separates from the base. In addition, the hydrophilic powder is washed away with moisture, and it becomes a major cause of makeup deterioration. In the past, when powder was blended into cosmetics, the powder that had been hydrophobized in advance was often used for blending.

There are numerous methods for the hydrophobization of powder used in cosmetics. For example, a powder hydrophobization method, in which higher fatty acids, higher alcohols, hydrocarbons, triglycerides, esters, silicones such as silicone oil and silicone resin, or fluorine compounds are used, has been practiced to cover the surface of hydrophilic powder. In particular, the powder hydrophobizing treatment, in which silicones are used as the surface-treating agent, can provide excellent hydrophobicity. Thus, numerous methods have been established so far (refer to patent literatures 1 and 2, for example). In recent years, a method in which a copolymer of acrylic acid and acrylic acid ester is used as the powder surface-treating agent is also known (refer to patent literature 3, for example).

On the other hand, the rinsability of cosmetics is also one of the important required characteristics. When the above-described conventional hydrophobized powder is blended, a longer-lasting makeup can be achieved. However, the makeup cannot be easily rinsed away with water, even when soap is used, because of the excellent hydrophobicity. Therefore, oily cleansing agents have been widely used, however, it also becomes necessary to wash away this oily cleansing agent with soap. Thus, the burden to users becomes high. When hydrophilic powder is blended to allow easy rinsing, the makeup easily deteriorates and the makeup is short-lasting as described above. Thus, it has been a very difficult theme to satisfy both the characteristics: long lasting makeup in use and easy rinsing after use.

Patent literature 1: Japanese Unexamined Patent Publication S60-163973
Patent literature 2: Japanese Unexamined Patent Publication S62-177070
Patent literature 3: Japanese Unexamined Patent Publication H8-337514

SUMMARY OF THE INVENTION

The present invention was made in view of the above-described problem, and the objects of the invention are to provide surface-treating agents that can provide excellent hydrophobicity to powder and can improve its rinsability, to provide surface-treated powders that are generated with the surface-treating agent, and to provide cosmetics that comprise the surface-treated powder.

The present inventors have diligently researched in view of the above-described problem and focused on the pH-responsive hydrophobicity-hydrophilicity change. The present inventors treated the surface of the powder with a polymer that comprised, as a constituent monomer, an acrylic derivative of a specific structure and found that the hydrophobicity-hydrophilicity of the surface-treated powder dramatically changes with the pH change. That is, the surface-treated powder with the above-described polymer shows excellent hydrophobicity in the acidic to neutral region, where general cosmetics are used. On the other hand, the surface of the powder becomes hydrophilic in the moderately basic conditions that are generated with soap water. As a result, we found that when the surface-treated powder was blended in cosmetics, the makeup was long-lasting; nevertheless, the makeup could be easily rinsed away with water by using soap, thus leading to the completion of the present invention.

The present inventors have diligently researched in view of the above-described problem, and focused on the pH-responsive hydrophobicity-hydrophilicity change. The present inventors used a polymer that comprised, as a constituent monomer, an acrylic derivative of a specific structure as the surface-treating agent of the powder and found that the hydrophobicity-hydrophilicity of the surface-treated powder dramatically changes with the pH change. That is, the powder treated with the above-described surface-treating agent shows excellent hydrophobicity in the acidic to neutral region, where general cosmetics are used. On the other hand, the surface of the powder becomes hydrophilic in the moderately basic conditions that are generated with soap water. As a result, when the treated powder is blended in cosmetics, the makeup is long-lasting; nevertheless, the makeup can be easily rinsed away with water by using soap. Thus, the present inventors found that the excellent hydrophobicity could be provided to the powder by treating the powder surface with the above-described surface-treating agent and that the rinsability could significantly be improved, thus leading to the completion of the present invention.

The first subject of the present invention is a surface-treating agent, which consists of a polymer comprising a monomer (A) represented by the general formula (1) described below as a constituent monomer.

[Formula 1]

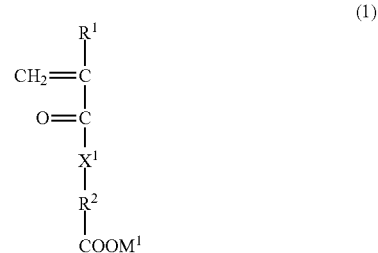

(wherein $R^1$ represents a hydrogen atom or an alkyl group having 1 to 3 carbon atoms, $R^2$ represents an alkylene group having 4 to 22 carbon atoms, $X^1$ represents an —NH— group or an oxygen atom, and $M^1$ represents a hydrogen atom or a monovalent inorganic or organic cation.)

In addition, it is preferable that the polymer of the surface-treating agent comprises the above-described monomer (A) equal to or more than 70 mole % of the total constituent monomers.

In addition, it is preferable that the polymer of the above-described surface-treating agent, further comprises a monomer (B), which is represented by any of the below-described general formulas (2) to (7) as a constituent monomer.

[Formula 2]

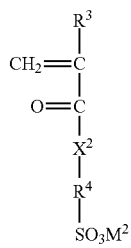

(2)

(wherein $R^3$ represents a hydrogen atom or an alkyl group having 1 to 3 carbon atoms, $R^4$ represents an alkylene group having 1 to 4 carbon atoms, $X^2$ represents an —NH— group or an oxygen atom, and $M^2$ represents a hydrogen atom or a monovalent inorganic or organic cation.)

[Formula 3]

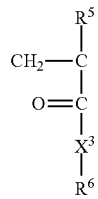

(3)

(wherein $R^5$ represents a hydrogen atom or an alkyl group having 1 to 3 carbon atoms, $R^6$ represents an alkyl group having 1 to 10 carbon atoms, a fluoroalkyl group, an aminoalkyl group, or a hydroxyalkyl group, and $X^3$ represents an —NH— group or an oxygen atom.)

[Formula 4]

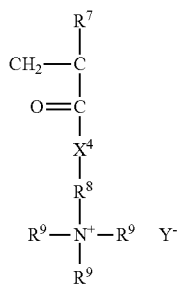

(4)

(wherein $R^7$ represents a hydrogen atom or an alkyl group having 1 to 3 carbon atoms, $R^8$ represents an alkylene group having 1 to 4 carbon atoms, $R^9$s may be the same or different and each represents a hydrogen atom or an alkyl group having 1 to 4 carbon atoms, $X^4$ represents an —NH— group or an oxygen atom, and $Y^-$ represents a monovalent organic or inorganic anion.)

[Formula 5]

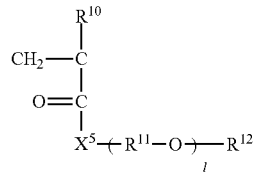

(5)

(wherein $R^{10}$ represents a hydrogen atom or an alkyl group having 1 to 3 carbon atoms, $R^{11}$ represents an alkylene group having 1 to 4 carbon atoms, $R^{12}$ represents a hydrogen atom or an alkyl group having 1 to 4 carbon atoms, $X^5$ represents an —NH— group or an oxygen atom, and/stands for an integer of 1 to 100.)

[Formula 6]

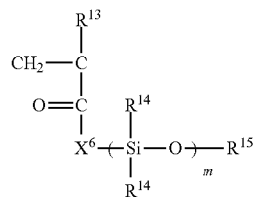

(6)

(wherein $R^{13}$ represents a hydrogen atom or an alkyl group having 1 to 3 carbon atoms, $R^{14}$s may be the same or different and each represents a hydrogen atom or an alkyl group having 1 to 4 carbon atoms, $R^{15}$ represents a hydrogen atom or an alkyl group having 1 to 4 carbon atoms, $X^6$ represents an —NH— group or an oxygen atom, and m stands for an integer of 1 to 100.)

[Formula 7]

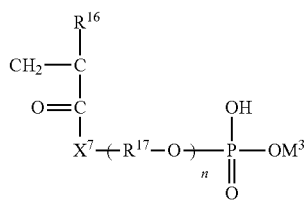

(7)

(wherein $R^{16}$ represents a hydrogen atom or an alkyl group having 1 to 3 carbon atoms, $R^{17}$ represents an alkylene group having 1 to 4 carbon atoms, $X^7$ represents an —NH— group or an oxygen atom, $M^3$ represents a hydrogen atom or a monovalent inorganic or organic cation, and n stands for an integer of 1 to 100.)

In addition, the mole ratio (A):(B) of the monomer (A) and the monomer (B) in the surface-treating agent is preferably within the range from 70:30 to 99.9:0.1.

The second subject of the present invention is surface-treated powder, which is coated with the surface-treating agent on the powder surface.

The amount of surface-treating agent coated on the powder, expressed in the mass ratio of the polymer to the powder, is preferably within the range from 3:97 to 40:60.

The third subject of the present invention is cosmetics, which comprises the surface-treated powder.

Effect of the Invention

The excellent hydrophobicity can be provided to the powder, and the rinsability can be significantly improved by treating the powder surface with the surface-treating agent of the present invention. Therefore, when the surface-treated powder treated with the surface-treating agent of the present invention is blended into cosmetics, the makeup can be easily rinsed away with water by using soap although the makeup is long-lasting.

DESCRIPTION OF THE PREFERRED EMBODIMENT

Figure 1:
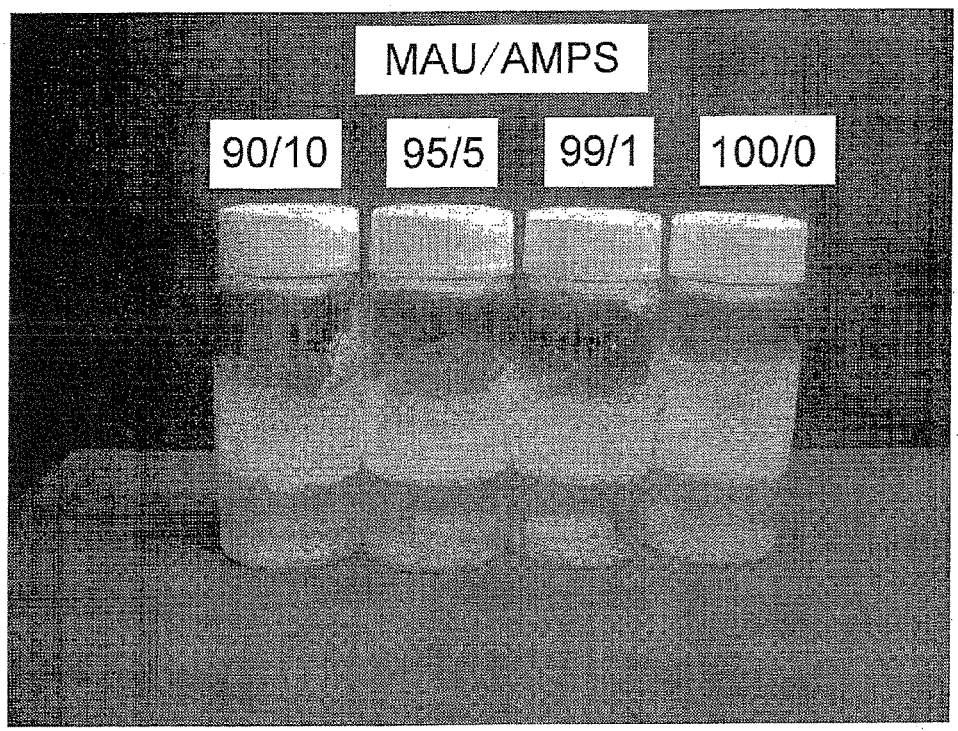
FIG. 1 shows a picture of pH 5 buffer solutions containing the surface-treated powder treated with various surface-treating agents (MAU homopolymer or MAU/AMPS copolymers) of the present invention.

In the following, the preferable mode for carrying out the present invention is described in detail.

The surface-treating agent of the present invention consists of a polymer which comprises a monomer (A) represented by the above-described general formula (1) as a constituent monomer.

The monomer (A) represented by the general formula (1) is a compound in which a fatty acid is attached to acrylic acid, alkyl-substituted acrylic acid, acrylamide, or alkyl-substituted acrylamide. In the general formula (1), $R^1$-represents a hydrogen atom or an alkyl group having 1 to 3 carbon atoms. When $R^1$ is an alkyl group, it can be either linear or branched. $R^1$ is preferably a hydrogen atom or a methyl group. In the general formula (1), $R^2$ is an alkylene group having 4 to 22 carbon atoms. The alkylene group can be either linear or branched. Examples of $R^2$ include an octylene group having 8 carbon atoms, an undecylene group having 11 carbon atoms, and a dodecylene group having 12 atoms. In addition, $R^2$ may include an aromatic ring or carbon-carbon double bonds in the structure, for example, $R^2$ may be a vinylene group, a methylphenylene group, or a vinylphenylene group. In the general formula (1), $X^1$ is an —NH— group or an oxygen atom, and it is preferably an —NH— group. In the general formula (1), $M^1$ is a hydrogen atom or a monovalent inorganic or organic cation. The monovalent inorganic or organic cation can be any cation so far as it can form a carboxylate salt. Examples of the monovalent inorganic cation include sodium ion, potassium ion, and lithium ion, and examples of the monovalent organic cation include ammonium ion, monoethanolammonium ion, and triethanolammonium ion. In addition, $M^1$ can be reversibly converted, after the preparation of the polymer, to the form of the carboxylic acid ($M^1$=hydrogen) or sodium salt ($M^1$=sodium) with an appropriate amount of dilute hydrochloric acid or dilute sodium hydroxide solution.

Examples of the monomer (A) of the present invention include 11-methacrylamidoundecanoic acid, 8-acrylamidooctanoic acid, 12-acrylamidododecanoic acid, 12-methacrylamidododecanoic acid, and 3-{4-[(methacryloxy)methyl]phenyl}acrylic acid. A polymer of the present invention may include one or more kind of the above-described monomer (A) as the constituent monomer.

A polymer of the present invention preferably comprises the above-described monomer (A) in equal to or more than 70 mole % of the total constituent monomers. If the content of the monomer (A) is less than 70 mole %, the effectiveness in the hydrophobicity-hydrophilicity adjustment is small, and desired characteristics may not be provided to the powder. The content of the monomer (A) is preferably equal to or more than 90 mole %. In the polymer of the present invention, the above-described monomer (A) may account for the total amount of the constituent monomer.

In the polymer of the present invention, a monomer (B) represented by any of the above-described general formulas (2) to (7) can be desirably used as a constituent monomer in addition to the above-described monomer (A).

The monomer represented by the general formula (2) is a compound in which an alkyl sulfonic acid is attached to acrylic acid, alkyl-substituted acrylic acid, acrylamide, or alkyl-substituted acrylamide. In the general formula (2), $R^3$ is a hydrogen atom or an alkyl group having 1 to 3 carbon atoms. When $R^3$ is an alkyl group, it can be either linear or branched. $R^3$ is preferably a hydrogen atom or a methyl group. In the general formula (2), $R^4$ is an alkylene group having 1 to 4 carbon atoms. The alkylene group can be either linear or branched. Examples of $R^4$ include a methylene group, an ethylene group, and a propylene group, and it is preferably an ethylene group or a propylene group. In the general formula (2), $X^2$ is an —NH— group or an oxygen atom, and it is preferably an —NH— group. In the general formula (2), $M^2$ is a hydrogen atom or a monovalent inorganic or organic cation. The monovalent inorganic or organic cation can be any cation so far as it can form a sulfonic acid. Examples of the monovalent inorganic cation include sodium ion, potassium ion, and lithium ion, and examples of the monovalent organic cation include ammonium ion, monoethanolammonium ion, and triethanolammonium ion. In addition, $M^2$ can be reversibly converted, after the preparation of a polymer, to the form of the sulfonic acid ($M^2$=hydrogen) or sodium salt ($M^2$=sodium) with an appropriate amount of dilute hydrochloric acid or dilute sodium hydroxide solution.

Examples of the monomer represented by the general formula (2) include 2-acrylamido-2-methylpropanesulfonic acid and potassium 3-methacryloxypropanesulfonate.

The monomer represented by the general formula (3) is a compound in which an alkyl group is attached to acrylic acid, alkyl-substituted acrylic acid, acrylamide, or alkyl-substituted acrylamide. In the general formula (3), $R^5$ is a hydrogen atom or an alkyl group having 1 to 3 carbon atoms. When $R^5$ is an alkyl group, it can be either linear or branched. $R^5$ is preferably a hydrogen atom or a methyl group. In the general formula (3), $R^6$ is an alkyl group having 1 to 10 carbon atoms, a fluoroalkyl group having equal to or more than one fluorine atom, an aminoalkyl group having equal to or more than one amino group, or a hydroxyalkyl group having equal to or more than one hydroxyl group. These alkyl groups can be either linear or branched. When $R^6$ is an alkyl group, the examples include a methyl group, an ethyl group, a pentyl group, an octyl group, a decyl group, and a 2-ethylhexyl group, and it is preferably a 2-ethylhexyl group. When $R^6$ is a fluoroalkyl group, the examples include a trifluoromethyl group, a trifluoroethyl group, and a tetrafluoropropyl group, and it is preferably a trifluoroethyl group or a tetrafluoropropyl group. When $R^6$ is an aminoalkyl group, the examples include an aminoethyl group and aminopropyl group, and an N,N-dimethylaminoethyl group, and it is preferably an N,N-dimethylaminoethyl group. When $R^6$ is a hydroxyalkyl group, the examples include a hydroxyethyl group, a hydroxypropyl group, and a dihydroxypropyl group, and it is preferably a hydroxyethyl group. In the general formula (3), $X^3$ is an —NH— group or an oxygen atom.

Examples of the monomer represented by the general formula (3) include 2-ethylhexyl acrylate, 2,2,2-trifluoropropyl acrylate, 2,2,3,3-tetrafluoropropyl methacrylate, 2-(N,N-dimethylamino)ethyl acrylate, 2-dimethylaminoethyl methacrylate, N-hydroxyethyl acrylate, and glycerol monomethacrylate.

The monomer represented by the general formula (4) is a compound in which an alkyl ammonium salt is attached to acrylic acid, alkyl-substituted acrylic acid, acrylamide, or alkyl-substituted acrylamide. In the general formula (4), $R^7$ is a hydrogen atom or an alkyl group having 1 to 3 carbon atoms. When $R^7$ is an alkyl group, it can be either linear or branched. $R^7$ is preferably a hydrogen atom or a methyl group. In the general formula (4), $R^8$ is an alkylene group having 1 to 4 carbon atoms. The alkylene group can be either linear or branched. Examples of $R^8$ include a methylene group, an ethylene group, and a propylene group, and it is preferably an ethylene group or propylene group. $R^9$s may be the same or different and each represents a hydrogen atom or an alkyl group having 1 to 4 carbon atoms. When $R^9$ is an alkyl group, it can be either linear or branched. $R^9$ is preferably a hydrogen atom or a methyl group. In the general formula (4), $X^4$ is an —NH— group or an oxygen atom. $Y^-$ is a monovalent organic or inorganic anion, and it can be any anion so far as it can form a quaternary ammonium salt. Examples of $Y^-$ include monovalent inorganic anions such as chloride ion, fluoride ion, and iodide ion; and monovalent organic anions such as sulfate ion, acetate ion, benzenesulfonate ion, and phosphate ion.

Examples of the monomer represented by the general formula (4) include N,N-dimethylaminoethyl acrylate methyl chloride and N,N-dimethylamino acrylamide methyl chloride.

The monomer represented by the general formula (5) is a compound, in which a (poly) alkylene oxide is attached to acrylic acid, alkyl-substituted acrylic acid, acrylamide, or alkyl-substituted acrylamide. In the general formula (5), $R^{10}$ is a hydrogen atom or an alkyl group having 1 to 3 carbon atoms. When $R^{10}$ is an alkyl group, it can be either linear or branched. $R^{10}$ is preferably a hydrogen atom or a methyl group. In the general formula (5), $R^{11}$ is an alkylene group having 1 to 4 carbon atoms, and the alkylene group can be either linear or branched. Examples of $R^{11}$ include a methylene group, an ethylene group, and a propylene group, and it is preferably an ethylene group or a propylene group. $R^{12}$ is a hydrogen atom or an alkyl group having 1 to 4 carbon atoms, and the examples include a hydrogen atom, a methyl group, and an ethyl group. $R^{12}$ is preferably a methyl group. In the general formula (5), $X^5$ is an —N— group or an oxygen atom. The letter l indicates the mole number of attached alkylene oxides, and it is an integer of 1 to 100.

Examples of the monomer represented by the general formula (5) include methoxypolyethylene glycol methacrylate.

The monomer represented by the general formula (6) is a compound in which polysiloxane is attached to acrylic acid, alkyl-substituted acrylic acid, acrylamide, or alkyl-substituted acrylamide. In the general formula (6), $R^{13}$ is a hydrogen atom or an alkyl group having 1 to 3 carbon atoms. When $R^{13}$ is an alkyl group, it can be either linear or branched. $R^{13}$ is preferably a hydrogen atom or a methyl group. In the general formula (6), $R^{14}$s may be the same or different and each represents a hydrogen atom or an alkyl group having 1 to 4 carbon atoms. When $R^{14}$ is an alkyl group, it can be either linear or branched. $R^{14}$ is preferably a hydrogen atom or a methyl group. $R^{15}$ is a hydrogen atom or an alkyl group having 1 to 4 carbon atoms, and the examples include a hydrogen atom, a methyl group, and an ethyl group. $R^{15}$ is preferably a hydrogen atom or a methyl group. In the general formula (6), $X^6$ is an —NH— group or an oxygen atom. The letter m indicates the mole number of attached siloxane groups, and it is an integer of 1 to 100.

Examples of the monomer represented by the general formula (6) include methacryloxy-modified silicones.

The monomer represented by the general formula (7) is a compound in which alkylphosphoric acid (salt) is attached to acrylic acid, alkyl-substituted acrylic acid, acrylamide, or alkyl-substituted acrylamide. In the general formula (7), $R^{16}$ is a hydrogen atom or an alkyl group having 1 to 3 carbon atoms. When $R^{16}$ is an alkyl group, it can be either linear or branched. $R^{16}$ is preferably a hydrogen atom or a methyl group. In the general formula (7), $R^{17}$ is an alkylene group having 1 to 4 carbon atoms, and the alkylene group can be either linear or branched. Examples of $R^{17}$ include a methylene group, an ethylene group, and a propylene group, and it is preferably an ethylene group or a propylene group. In the general formula (7), $X^7$ is an —NH— group or an oxygen atom. The letter n indicates the mole number of attached alkylene oxides, and it is an integer of 1 to 100. In the general formula (7), $M^3$ is a hydrogen atom or a monovalent inorganic or organic cation. The monovalent inorganic or organic cation can be any cation so far as it can form a phosphate. Examples of the monovalent inorganic cation include sodium ion, potassium ion, and lithium ion, and examples of the monovalent organic cation include ammonium ion, monoethanolammonium ion, and triethanolammonium ion. In addition, $M^3$ can be reversibly converted, after the preparation of a polymer, to the form of the phosphoric acid ($M^3$=hydrogen) or sodium salt ($M^3$=sodium) with an appropriate amount of dilute hydrochloric acid or dilute sodium hydroxide solution.

Examples of the monomer represented by the general formula (7) include 2-methacryloxyethyl phosphoric acid.

The polymer of the present invention may include one or more kind of any monomer (B) represented by the above-described general formulas (2) to (7) as the constituent monomer.

The polymer of the present invention preferably comprises the above-described monomer (B) in 1 to 30 mole % of the total constituent monomers. If the content of the monomer (B) is less than 1 mole %, the blending effect cannot be achieved. If the content of the monomer (B) is more than 30 mole %, the relative content of monomer (A) becomes small. As a result, desired characteristics may not be provided to the powder.

The polymer of the present invention can comprise a monomer other than the above-described monomers (A) and (B) as the constituent monomer so far as the effect of the present invention is not undermined. The content equal to or less than 30 mole % of the total constituent monomers is satisfactory, and the content can be, for example, about 1 to about 20 mole %. Examples of the monomer include acrylamide, methacrylamide, N-vinylpyrrolidone, $\epsilon$-caprolactam, vinylalcohol, maleic anhydride, diallyldimethylammonium chloride, and styrene.

The polymer of the present invention can be obtained by polymerizing various monomers, including the above-described monomers, by publicly known polymerization methods. For example, homogeneous solution polymerization, heterogeneous solution polymerization, emulsion polymerization, inverse emulsion polymerization, bulk polymerization, suspension polymerization, and precipitation polymerization can be used. For example, in the case of homogeneous solution polymerization, the polymer of the present invention can be obtained by dissolving various monomers in a solvent, adding a radical polymerization initiator under a nitrogen atmosphere, and heating the solution with stirring. In addition, the polymer of the present invention can be obtained by the post-modification in which functional groups are attached to polyacrylic acid or polyacrylamide.

As the solvent for the polymerization, any solvent can be used so far as various monomers can be dissolved or suspended and it is an organic solvent containing no water. Examples include alcohol solvents, such as methanol, ethanol, propyl alcohol, isopropyl alcohol, and butyl alcohol; hydrocarbon solvents, such as hexane, heptane, octane, isooctane, decane, and liquid paraffin; ether solvents, such as dimethyl ether, diethyl ether, and tetrahydrofuran; ketone solvents, such as acetone and methyl ethyl ketone; ester solvents, such as methyl acetate, ethyl acetate, and butyl acetate; chlorine solvents, such as methylene chloride, chloroform, and carbon tetrachloride; dimethylformamide; diethylformamide; dimethyl sulfoxide; and dioxane. More than one kind of these solvents can be mixed for use. It is usually preferable to select a solvent that has a higher boiling point than the initiation temperature of the polymerization initiator.

The polymerization initiator is not limited in particular so far as it can initiate radical polymerization, and examples include peroxides such as benzoyl peroxide, azo compounds such as azobisisobutyronitrile (AIBN) and dimethyl 2,2'-azobis(isobutyrate), and persulfate polymerization initiators such as potassium persulfate and ammonium persulfate. The polymerization can be conducted, without depending on a polymerization initiator, by a photochemical reaction, radiation, or the like. The polymerization temperature should be equal to or more than the polymerization initiation temperature of each polymerization initiator. For example, about 50 to about 70° C. is usually suitable for the peroxide polymerization initiator.

The polymerization time is not limited in particular, and it is usually about 30 minutes to about 24 hours. When a polymer with a relatively high molecular weight is desirable, the desirable reaction time is about 24 hours. If the reaction time is too short, the unreacted monomer remains and the molecular weight may turn out to be relatively small. The average molecular weight of the polymer of the present invention is not limited in particular. If the degree of polymerization is more than that of oligomers, the desired effect can be achieved. However, the average molecular weight is preferably about 3000 to about 100 thousand. In polymerization by mixing more than one kind of monomer, a copolymer in which various monomers are randomly added can usually be obtained.

The surface-treated powder of the present invention is characterized in that the above-obtained polymer is coated on the powder surface.

The polymer used in the present invention has carboxyl groups, which are derived from the above-described monomer (A), on the side chains of the polymer. The carboxyl group changes to a hydrophobic carboxylic acid (—COOH) under acidic to neutral conditions and changes to a hydrophilic carboxylate ion (—COO$^-$M$^-$) under basic conditions. Therefore, the powder the surface of which is treated with this polymer, for example, is considered to be hydrophobic in the acidic to neutral environment and hydrophilic in the basic environment. As a result, the pH-responsive hydrophobicity-hydrophilicity change is exhibited.

When the thus obtained surface-treated powder is blended in cosmetics, the cosmetics show hydrophobicity in the acidic to neutral region, where cosmetics are normally used, achieving long-lasting makeup. Nevertheless, when the surrounding becomes moderately basic with soap, the treated powder surface becomes hydrophilic and the makeup can be easily rinsed away.

The above-described monomer (B) is not easily affected by pH, and the monomer shows a stable hydrophilic or hydrophobic property in the wide range of pH. Therefore, if a polymer is prepared by appropriately adjusting the ratio of the above-described monomer (A) and monomer (B) as the constituent monomers, the desirable hydrophobicity-hydrophilicity balance, which is provided to the powder, can be achieved. For example, it is possible to increase the hydrophilicity by combining a monomer (B) represented by the general formula (2) with the above-described monomer (A). On the contrary, it is possible to increase the hydrophobicity by combining a monomer (B) represented by the general formula (6) with the above-described monomer (A). In addition, it is possible to increase the adsorption of powder to the polymer by utilizing an appropriate amount of the above-described monomer (B).

In the polymer used in the present invention, the mole ratio (A):(B) of the monomer (A) and the monomer (B) should preferably be adjusted within the range from 70:30 to 99.9:0.1. If the content of the monomer (A) is less than the ratio of 70:30, the treated powder will become hydrophilic, and satisfactory hydrophobicity may not be achieved. On the other hand, if the content of the monomer (A) is more than the ratio of 99.9:0.1, it will become difficult to adsorb a polymer on the powder surface, and the stability of the powder may be negatively affected.

The powder used in the present invention is not limited in particular, and examples include inorganic powders, such as silicic acid, silicic anhydride, magnesium silicate, talc, kaolin, mica, bentonite, titanated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine blue, iron blue, chromium oxide, chromium hydroxide, carbon black, and composites thereof; and organic powders, such as polyamide, polyester, polyethylene, polypropylene, polystyrene, polyurethane, vinyl resin, epoxy resin, polycarbonate resin, divinylbenzene/styrene copolymer, copolymers consisting of more than one kind of monomer of the above-described compounds, celluloid, acetylcellulose, cellulose, polysaccharides, protein, CI pigment yellow, CI pigment orange, and CI pigment green. The shape of powder can be any shape, for example, plate, agglomerate, scaly shape, sphere, porous sphere, and the particle size is also not limited in particular.

In the preparation of the surface-treated powder of the present invention, the surface treatment of the powder can be conducted by any normal treatment method; thus, the method is not limited in particular. Examples of the treatment of the powder with the above-described polymer include the method in which the polymer is dissolved in a suitable solvent such as ethyl alcohol, the powder is mixed into the solution and stirred, and then the solvent is removed; and the method in which a polymer dissolved in a non-volatile oil such as a higher alcohol is directly mixed into the powder with stirring. When the surface-treated powder of the present invention is blended into cosmetics, the polymer may be directly mixed, with stirring, into the powder base during the production process of the cosmetics.

In the present invention, when the powder is treated with the above-described polymer, it is necessary to pay attention to the zeta potential of the powder. Here, the zeta potential of the powder indicates a difference between the potential of the outermost surface (sliding surface) of the moving layer, which is in close contact with the solid phase, and the potential in the solution during the relative movement of the solid phase and the liquid phase. When the solution is at near-neutral pH, the zeta potential of titanium oxide and silica is negative; on the contrary, the zeta potential of zinc oxide and alumina is positive. When a powder with the positive zeta potential, such as zinc oxide or alumina, is treated with the normal method, the carboxylic acid site, which is important for pH response, is countered by the positive charge of the powder surface. As a result, the obtained surface-treated powder may not exhibit a pH response. In order to provide pH response capability to the powder, it is necessary to change the zeta potential of the powder surface to be negative by treating the powder surface with an inorganic compound or an organic compound possessing a negative charge, such as silica or polystyrene sulfonic acid. Examples of such a treatment method include the method in which the powder is dispersed in a water glass solution, and silica is deposited on the surface by the dropwise addition of an acid; and the method in which the powder is dispersed in an aqueous solution of polystyrene sulfonic acid, and water is evaporated.

In the surface-treated powder of the present invention, the mass ratio of the coated polymer to the powder (polymer:powder) is preferably 3:97 to 40:60 and more preferably 5:95 to 30:70. If the amount of coated polymer is less than 3:97, desired characteristics may not be provided to the powder. If the amount of coated polymer is more than 40:60, the feeling during the use of the cosmetics may be negatively affected.

The cosmetics of the present invention are characterized in that the above obtained surface-treated powder is comprised in the cosmetics. The blending amount of the surface-treated powder is preferably equal to or more than 3 mass % of the total amount of cosmetics and more preferably 5 to 95 mass %. If the blending amount is less than 3 mass %, the effect of the present invention may not be achieved.

To the cosmetics of the present invention, normally used cosmetic ingredients, such as water, oil, powder (untreated), surfactant, fluorine compounds, resin, thickener, preservative, perfume, ultraviolet absorber, moisturizer, bioactive component, salts, solvent, antioxidant, chelating agent, neutralizing agent, and pH adjusting agent may be blended in addition to the above-described surface-treated powder so far as the effect of the present invention is not undermined.

The forms of cosmetics in the present invention are not limited in particular. Their examples include makeup cosmetics such as foundation, white face powder, lipstick, eye shadow, cheek color, mascara, and eye liner; sunscreen; foundation cream; and hair cream.

Example 1

Examples of the present invention will hereinafter be described. However, the present invention is not limited by these examples.

Initially, the polymer synthesis methods of the present invention will be described.

Synthesis Example

11-Methacrylamidoundecanoic Acid (MAU) Homopolymer

[Formula 8]

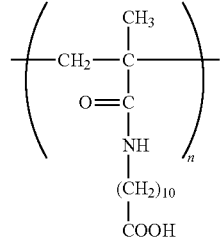

Into a mixed solvent of 32.4 mL of methanol and 3.6 mL water (methanol/water=9/1) were dissolved 5.244 g (18 mmol) of sodium 11-methacrylamidoundecanoate (NaMAU) and 7.4 mg (0.045 mmol) of azobisisobutyronitrile. The solution was deaerated by bubbling argon for 30 minutes, the container was covered with a septum, and the polymerization was conducted by heating the solution at 60° C. for 12 hours. After the completion of the polymerization reaction, the reaction solution was dropwise added into a large excess of ether, and the resulting precipitate was collected by filtration under suction. This precipitate was dissolved in water, dialyzed against pure water for 1 week, and 2.64 g of NaMAU homopolymer was obtained by freeze-drying (yield: 50.40%).

Into water was dissolved 1.10 g of the collected NaMAU homopolymer, and the pH was adjusted to 4 with hydrochloric acid. This solution was dialyzed against water of pH 5 for 1 week, and 0.97 g of 11-methacrylamidoundecanoic acid (MAU) homopolymer was obtained by freeze-drying.

Synthesis Example 2

11-Methacrylamidoundecanoic Acid (MAU)/2-acrylamido-2-methylpropanesulfonic Acid (AMPS) Copolymer (MAU/AMPS=95/5)

[Formula 9]

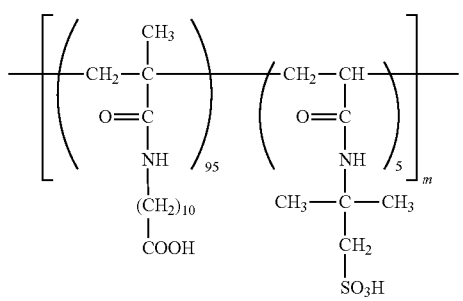

Into a mixed solvent of 32.4 mL of methanol and 3.6 mL water (methanol/water=9/1) were dissolved 4.9823 g (17.1 mmol) of sodium 11-methacrylamidoundecanoate (NaMAU), 186.5 mg (0.9 mmol) of 2-acrylamido-2-methylpropanesulfonic acid (AMPS), 39.6 mg (0.99 mmol) of sodium hydroxide, and 7.4 mg (0.045 mmol) of azobisisobutyronitrile. The solution was deaerated by bubbling argon for 30 minutes, the container was covered with a septum, and the polymerization was conducted by heating the solution at 60° C. for 12 hours. After the completion of the polymerization reaction, the reaction solution was dropwise added into a large excess of ether, and the resulting precipitate was collected by filtration under suction. This precipitate was dissolved in water, dialyzed against pure water for 1 week, and 2.78 g of random NaMAU/AMPS copolymer (95/5) was obtained by freeze-drying (yield: 53.71%).

Into water was dissolved 1.54 g of the collected NaMAU/AMPS copolymer, and the pH was adjusted to 4 with hydrochloric acid. This solution was dialyzed against water of pH 5 for 1 week, and 0.97 g of random MAU/AMPS copolymer (95/5) was obtained by freeze-drying.

In the following section, the surface treatment method of powder with the surface-treating agent of the present invention will be described.

Example 2, and Powder Treatment Example 1. Then the present inventors evaluated the water solubility of the treated powders under the acidic (pH 5) and the basic (pH 10) conditions. In addition, similar tests were conducted using silicones and acrylic acid/acrylic acid ester copolymer, which are traditional hydrophobizing surface-treating agents, as comparative examples. Evaluation results are shown in Table 1 and FIGS. 1 and 2. The evaluation method was as follows.

Water Solubility of Treated Powder

Each of 0.1 g titanium oxide powder that has been surface-treated with various surface-treating agents and a 30 mL aqueous buffer solution of pH 5 or pH 10 were placed in a vial, mixed for 1 minute by stirring with a magnetic stirrer, and allowed to stand. Then the condition of each solution was checked.

o: Powder evenly dissolved in water, and it formed a white cloudy solution.

x: Powder did not dissolve in water, and it separated on the water surface.

TABLE 1

|  |  | Surface-treating agent | Water solubility of powder | |
|---|---|---|---|---|
|  |  |  | pH 5 | pH 10 |
| Example | 1-1 | MAU/AMPS copolymer (MAU/AMPS = 90/10) | X | ○ |
|  | 1-2 | MAU/AMPS copolymer (MAU/AMPS = 95/5) | X | ○ |
|  | 1-3 | MAU/AMPS copolymer (MAU/AMPS = 99/1) | X | ○ |
|  | 1-4 | MAU homopolymer (MAU/AMPS = 100/0) | X | ○ |
| Comperative | 1-1 | Methylhydrogenpolysiloxane | X | X |
| Example | 1-2 | Dimethyldichlorosilane | X | X |
|  | 1-3 | Octyl acrylamide/acryl resin copolymer *1 | X | X |
|  | 1-4 | Vinyl acetate/crotonic acid copolymer | X | X |

*1: Darmacryl-79 (Kanebo-NSC)

Powder Treatment Example 1

Into 500 mL of ethanol were dissolved 45 g of a polymer prepared by the above-described Synthesis Example 1 or Synthesis Example 2 and 15 g of stearic acid. Into this solution was blended 240 g of titanium oxide and dispersed, and the ethanol was evaporated with an evaporator. The obtained agglomerate was pulverized, and the surface-treated powder was obtained.

The obtained treated powder was dissolved, by mixing, into a buffer solution of pH 5 and a buffer solution of pH 10 in a powder-solution ratio of 1:100. This solution was centrifuged to isolate the powder, and the residual liquid was removed by drying. The obtained powder was analyzed by elemental analysis to measure the degree of polymer coating, and the content of polymer was found to be 15 mass % of the total powder, and the content of stearic acid was 5 mass % of the total powder.

Examples 1-1 to 1-4 and Comparative Examples 1-1 to 1-4

Figure 2:
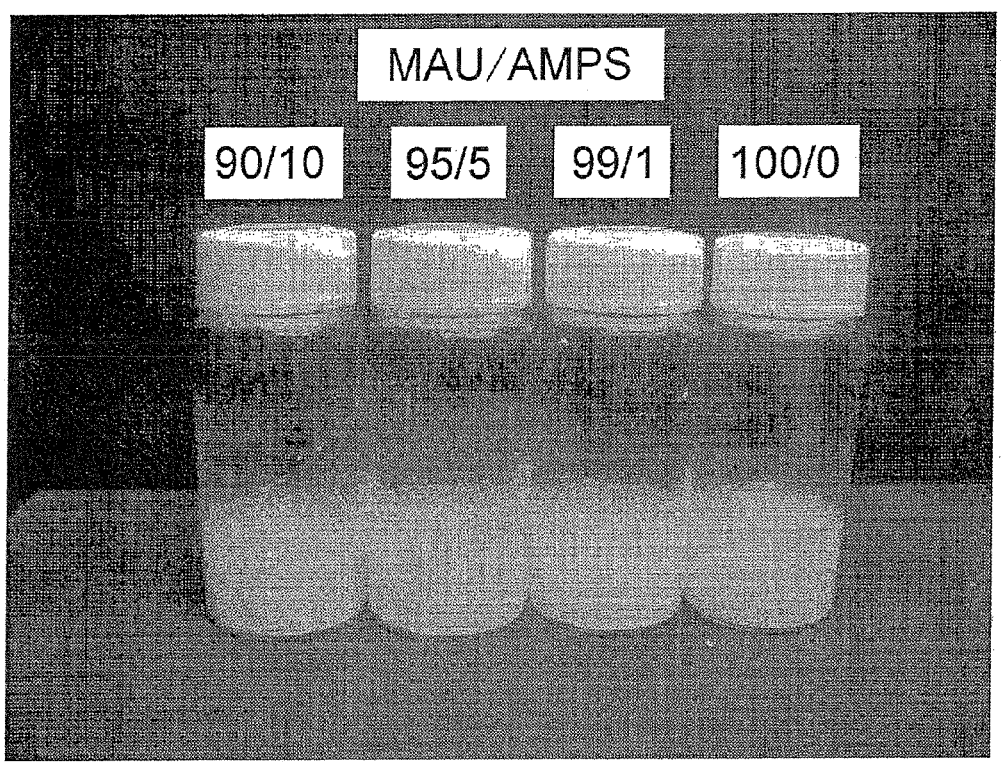
FIG. 2 shows a picture of pH 10 buffer solutions containing the surface-treated powder treated with various surface-treating agents (MAU homopolymer or MAU/AMPS copolymers) of the present invention.

In order to investigate the properties of the powder that has been surface-treated with the polymer of the present invention, the present inventors prepared titanium oxide powders that were surface-treated with various polymers according to the above-described Synthesis Example 1, Synthesis As shown in Table 1 and FIGS. 1 and 2, the surface-treated powder with MAU homopolymer or MAU/AMPS copolymer of the present invention (Examples 1-1 to 1-4) did not dissolve in water under acidic condition (pH 5). Thus, the powder was found to have excellent hydrophobicity under acidic condition (pH 5). On the other hand, under basic condition (pH 10), the treated powder evenly dissolved in water. Thus, the powder was found to change to hydrophilic under basic condition (pH 10). That is to say, when the powder treated with the polymer of the present invention is blended into cosmetics, the powder has excellent hydrophobicity in the acidic to neutral region, in which normal cosmetics are used; as a result, the makeup is long-lasting. Nevertheless, the powder can be easily rinsed away with water under the moderately basic condition that is generated with soap because the powder surface changes to hydrophilic.

In contrast, the powder that is surface-treated with silicones or acrylic acid/acrylic acid ester copolymer, which is the traditionally used hydrophobizing agent in cosmetic powder (Comparative Examples 1-1 to 1-4), dissolved in water neither under acidic condition (pH 5) nor under basic condition (pH 10). Thus, when the powder treated with the traditional surface-treating agent is blended in cosmetics, long-lasting makeup could be achieved. However, it is difficult to rinse away with soap water because excellent hydrophobicity is maintained even under basic conditions.

Synthesis Example 3

3-{4-[(Methacryloxy)methyl]phenyl}acrylic acid (MMPA) homopolymer

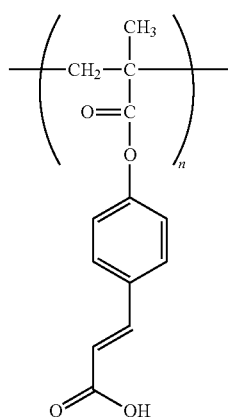

[Formula 10]

1) Synthesis of MMPA Monomer

Figure 3:
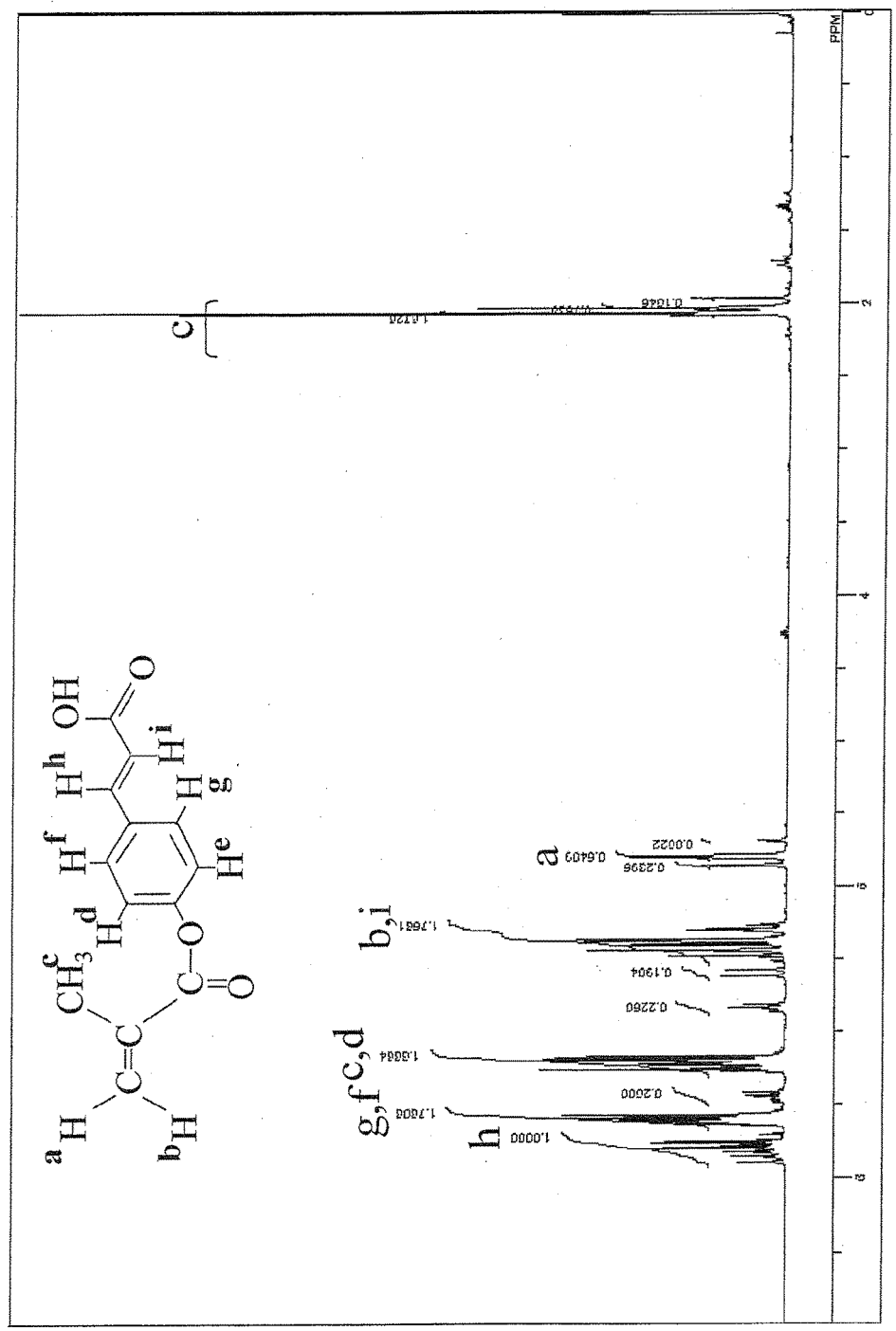
FIG. 3 shows the results of NMR measurement of a surface-treating agent (MMPA homopolymer) of the present invention.

In 25 g of acetone were dissolved 2.46 g (15 mmol) of 4-hydroxycinnamic acid and 0.005 g of butylhydroxytoluene. To the solution was dropwise added 1.57 g (15 mmol) of methacryloyl chloride, and the mixture was stirred at room temperature for 3 hours. After the completion of the reaction, to the solution was dropwise added 1.67 g of triethylamine, and then 100 g of 0.015N dilute hydrochloric acid solution was added. The resulting precipitate was collected by filtration under suction. The precipitate was washed with water and dried at 30° C. under reduced pressure, whereby 2.09 g of MMPA monomer was obtained (yield: 60%). By the NMR analysis of the product, the formation of MMPA monomer was confirmed. The NMR analysis results are shown in FIG. 3.

2) Polymerization of MMPA Monomer

In 100 g of tetrahydrofuran was dissolved 2.01 g (9 mmol) of the above-obtained MMPA monomer, and nitrogen was bubbled through the solution for 40 minutes. Subsequently, 0.038 g (0.23 mmol) of azobisisobutyronitrile that was dissolved in 10 g of tetrahydrofuran was dropwise added to the solution. After nitrogen was bubbled through the solution for 10 minutes, the polymerization was conducted by stirring at 60° C. for 24 hours. After the completion of the polymerization reaction, the reaction solution was concentrated with an evaporator, and the precipitate was removed by the addition of ethyl acetate. The solution was concentrated again with an evaporator. By drying at 30° C. under reduced pressure, 1.64 g of MMPA homopolymer was obtained (yield: 82%).

Powder Treatment Example 2

In 50 mL of tetrahydrofuran was dissolved 1 g of MMPA homopolymer, which was prepared in the above-described Synthesis Example 3. In this solution, 9 g of titanium oxide was blended and dispersed, and tetrahydrofuran was evaporated with an evaporator. The obtained agglomerate was pulverized, whereby the surface-treated powder was obtained.

Example 1-5

The present inventors prepared titanium oxide powder that was surface-treated with MMPA homopolymer according to the above-described Powder Treatment Example 2. The obtained treated powder was blended and dispersed in buffer solutions of pH 5 and pH 10 in a powder-solution ratio of 1:100. Thus, the water solubility of the treated powder under acidic condition (pH 5) and basic condition (pH 10) was evaluated. The results are shown in FIG. 4.

Figure 4:
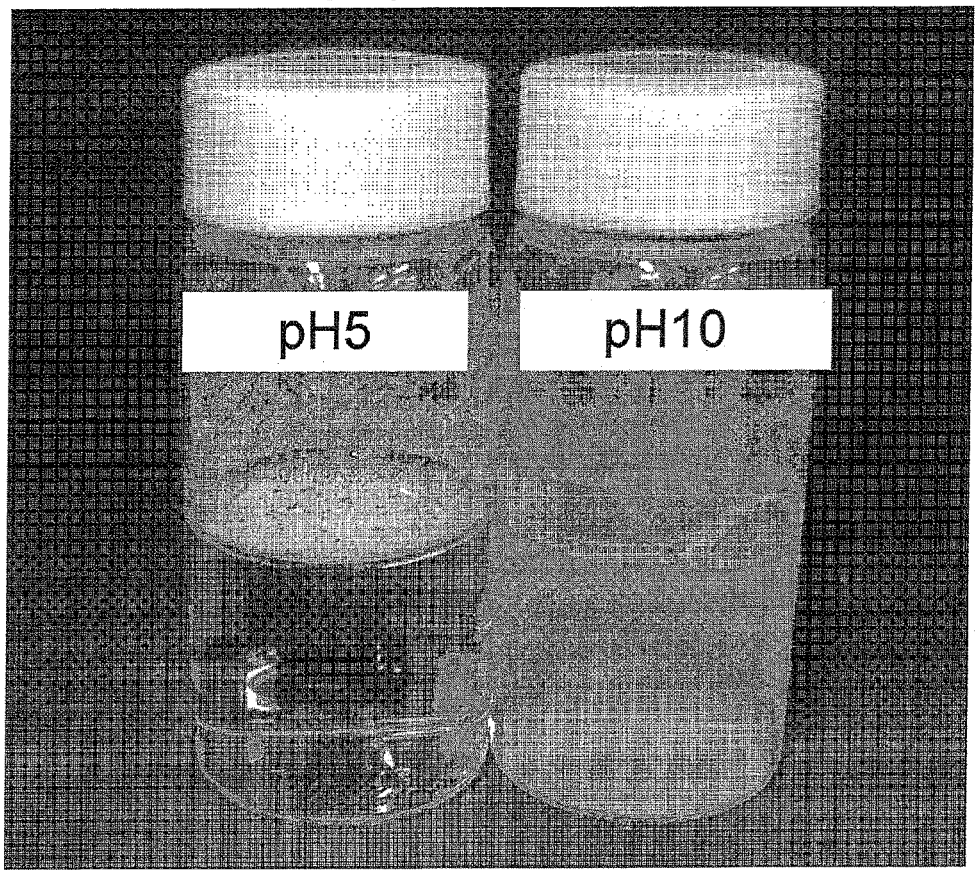
FIG. 4 shows a picture of pH 5 and pH 10 buffer solutions containing the surface-treated powder treated with a surface-treating agent (MMPA homopolymer) of the present invention.

As shown in FIG. 4, surface-treated powder with MMPA homopolymer of the present invention (Example 1-5) did not dissolve in water under acidic condition (pH 5). On the other hand, under basic condition (pH 10), the treated powder evenly dissolved in water. Thus, it was confirmed that the powder changed from hydrophobic to hydrophilic by the change of pH.

Subsequently, the present inventors conducted infrared spectroscopic measurement of the MMPA polymer of the above-described Synthesis Example 3 under the condition of no treatment and under the condition of 1 M NaOH solution treatment. The results are shown in FIG. 5.

Figure 5:
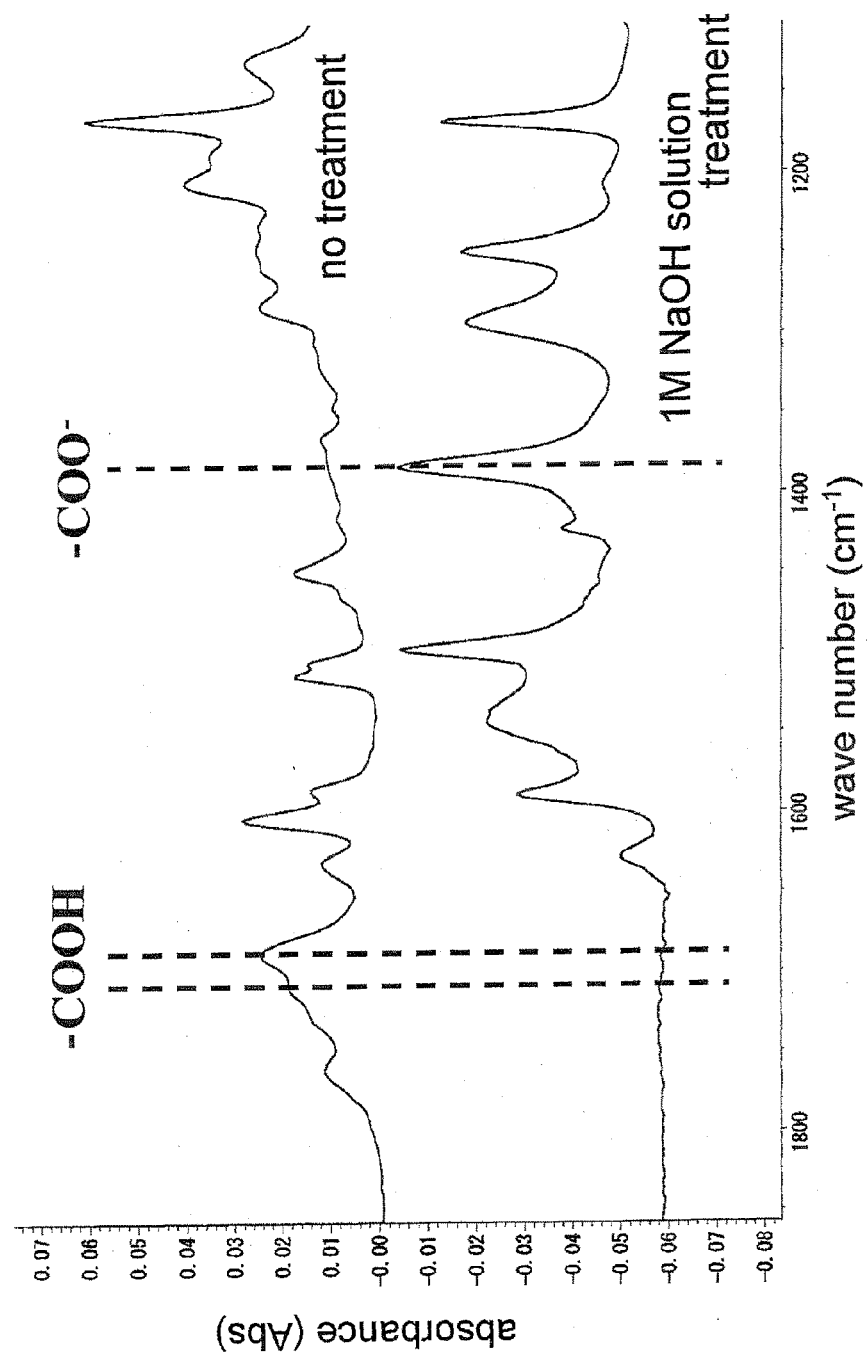
FIG. 5 shows the results of infrared spectroscopic measurement of a surface-treating agent (MMPA homopolymer) of the present invention under the untreated and treated (with 1 M NaOH solution) conditions.

As shown in FIG. 5, the MMPA homopolymer of the present invention shows peaks due to carboxylic acid (—COO⁻) under the condition of no treatment. Under the condition of 1 M NaOH solution treatment, the above-described peaks due to the carboxylic acid disappear, and the appearance of a new carboxylate ion (—COO⁻) peak was identified. According to the results, the polymer of the present invention is in the form of hydrophobic carboxylic acid under acidic to neutral conditions, and it changes to the hydrophilic carboxylate ion under basic conditions. As a result, the pH-responsive hydrophobicity-hydrophilicity change is considered to take place.

Example 2

The present inventors prepared cosmetics in which the surface-treated powder with the polymer of the present invention is blended, and the evaluation was conducted.

Example 2-1

In 1000 mL of ethanol were dissolved 34.5 g of the MAU/AMPS copolymer (MAU/AMPS=95/5), which was prepared according to the above-described Synthesis Example 2, and 34.5 g of stearic acid. In this solution, 85 g of talc, 50.8 g of sericite, 10 g of titanium oxide, 6 g of nylon powder, 0.4 g of black iron oxide, 5.8 g of yellow iron oxide, and 2 g of red iron oxide were blended and dispersed, and the ethanol was evaporated with an evaporator. The obtained agglomerate was pulverized, and the surface-treated powder of Example 2-1 was obtained.

Example 2-2

| Powder type foundation | Amount (mass %) |
| --- | --- |
| (1) Surface treated powder in Example 2-1 | 86.6 |
| (2) Liquid paraffin | 4.0 |
| (3) Octyldodecyl myristate | 3.0 |
| (4) Sorbitan isostearate | 3.0 |
| (5) Octyldodecanol | 3.0 |
| (6) Preservative | 0.1 |
| (7) Disinfectant | 0.1 |
| (8) Antioxidant | 0.1 |
| (9) Perfume | 0.1 |

(Manufacturing method) (2)-(6) are heated and dissolved, then (1), (7)-(9) are added thereto. This was mixed with Henschel mixer, the powder type foundation was obtained.

Above obtained powder type foundation was excellent in long-lasting, and able to be easily rinsed away with water by using soap.

Execution Example 2-3

| Two-layers type W/O sunscreen | Amount(mass %) |
| --- | --- |
| (1)Talc | 10.0 |
| (2)Surface treated titania in Example 1-1 | 10.0 |
| (3)Isocetyl octate | 5.0 |
| (4)Decamethylcyclopentasiloxane | 26.8 |
| (5)Dimethylpolysiloxane | 10.0 |
| (6)POE modified dimethylpolysiloxane | 2.0 |
| (7)Ion-exchanged water | 28.0 |
| (8)1,3-Butylene glycol | 8.0 |
| (9)Preservative | 0.1 |
| (10)Perfume | 0.1 |

(Manufacturing method) (3)-(6) were heated and mixed at 70° C. as oil phase. Separately, (8) and (9) were dissolved into (7) as aqueous phase. The powder of (1) and (2) was added into the oil phase, and dispersed with the homomixer. The aqueous phase was added into this, and emulsified with the homo mixer. In addition, (10) was mixed with them, and filled into the container.

Above obtained two-layers type W/O sunscreen was excellent in long-lasting, and able to be easily rinsed away with water by using soap.

Example 2-4

| W/O type foundation | Amount (mass %) |
| --- | --- |
| (1) Surface treated powder in Example 2-1 | 20.32 |
| (2)Liquid paraffin | 5.0 |
| (3)Decamethylcyclopentasiloxane | 29.0 |
| (4)POE modified dimethylpolysiloxane | 4.5 |
| (5)Ion-exchanged water | 36.0 |
| (6)1,3-Butylene glycol | 5.0 |
| (7)Preservative | 0.1 |
| (8)Perfume | 0.08 |

(Manufacturing method) (2)-(4) were heated and dissolved at 70-80° C. (This was oil phase). (6) and (7) were dissolved into (5) (This was aqueous phase). The oil phase was added into (1), and mixed with homomixer. (8) was mixed with them, and water was added thereto. This was filled it to the container.

Above obtained W/O type foundation was excellent in long-lasting, and able to be easily rinsed away with water by using soap.

Example 2-5

| Lipstick | Amount(mass %) |
| --- | --- |
| (1)Surface treated titania in Example 1-3 | 10.0 |
| (2)Red pigment No. 201 | 0.6 |
| (3)Red pigment No. 202 | 1.0 |
| (4)Red pigment No. 223 | 0.2 |
| (5)Candelilla wax | 9.0 |
| (6)Solid paraffin | 8.0 |
| (7)Beeswax | 5.0 |
| (8)Carnauba wax | 5.0 |
| (9)Lanolin | 11.0 |
| (10)Castor oil | 23.2 |
| (11)Cetyl 2-ethylhexanoate | 17.0 |
| (12)Isopropyl myristic acid ester | 10.0 |
| (13)Antioxidant | q.s. |
| (14)Perfume | q.s. |

(Manufacturing method) (1)-(3) were mixed with a part of (10), and treated with a roller (This was pigment part). (4) were dissolved into a part of (10) (This was dye part). (5)-(13) were mixed, heated and dissolved, then the pigment part and dye part were added thereto. These were dispersed uniformly with homomixer. This was poured in mold, cooled quickly, and shaped as stick.

Above obtained lipstick was excellent in long-lasting, and able to be easily rinsed away with water by using soap.

Example 2-6

| Oil type stick foundation | Amount(mass %) |
| --- | --- |
| (powder part) | |
| (1)Surface treated powder in Example 2-1 | 50.0 |
| (Oil phase) | |
| (2)Solid paraffin | 3.0 |
| (3)Microcrystalline Wax | 7.0 |
| (4)Petrolatum | 15.0 |
| (5)Dimethylpolysiloxane | 3.0 |
| (6)Squalane | 5.0 |
| (7)Isopropyl palmitate | 17.0 |
| (8)Antioxidant | q.s. |
| (9)Perfume | q.s. |

(Manufacturing method) (2)-(8) were dissolved at 85° C., and enough mixed powder part were added thereto with stirring. Next, this was dispersed by grinding with colloid mill. (9) was added thereto. After degassing, this was poured into the container at 70° C. This was cooled, and the cosmetic was obtained.

Above obtained stick foundation was excellent in long-lasting, and able to be easily rinsed away with water by using soap.

Example 3

The present invention will hereinafter be described in further detail by other examples. However, the present invention is not limited by these examples. The molecular weight was determined with size exclusion chromatography, HLC-8220 GPC (Tosoh Corporation). As the column, Shodex Asahipak GF-7M HQ (Showa Denko K.K.) was used, and as the mobile phase, methanol containing 100 mM of lithium perchlorate was used. As the standard material, polyethylene oxide was used, and the obtained weight average molecular weight is based on polyethylene oxide.

Example 3-1

11-Methacrylamidoundecanoic Acid (MAU) Homopolymer

In 224.69 g of methanol were dissolved 75.0 g (278.49 mmol) of 11-methacrylamidoundecanoic acid (MAU) and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 45.6 g of MAU homopolymer was obtained (yield: 60.8%). The weight average molecular weight was 66000.

Example 3-2

11-Methacrylamidoundecanoic Acid (MAU) Homopolymer

In 224.07 g of methanol were dissolved 75.0 g (278.49 mmol) of 11-methacrylamidoundecanoic acid (MAU) and 0.93 g (5.66 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 64.9 g of MAU homopolymer was obtained (yield: 86.5%). The weight average molecular weight was 61000.

Example 3-3

12-Methacrylamidododecanoic Acid (MAD) Homopolymer

In 120.0 g of methanol was dissolved 40.0 g (141.34 mmol) of 12-methacrylamidododecanoic acid (MAD) and 0.58 g (3.53 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of diethyl ether, and the resulting precipitate was collected by filtration under suction. After drying under reduced pressure, 124.15 g of MAD homopolymer was obtained (yield: 60.4%). The weight average molecular weight was 33000.

Example 3-4

12-Acrylamidododecanoic Acid (AAD) Homopolymer

In 360.0 g of methanol were dissolved 40.0 g (148.70 mmol) of 12-acrylamidododecanoic acid (AAD) and 0.61 g (3.71 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of diethyl ether, and the resulting precipitate was collected by filtration under suction. After drying under reduced pressure, 27.51 g of AAD homopolymer was obtained (yield: 68.8%). The weight average molecular weight was 44000.

Example 3-5

11-Methacrylamidoundecanoic Acid (MAU)/2-acrylamido-2-methylpropanesulfonic Acid (AMPS) Copolymer (99/1)

In 223.92 g of methanol were dissolved 74.23 g (275.63 mmol) of 11-methacrylamidoundecanoic acid (MAU), 0.77 g (3.72 mmol) of 2-acrylamido-2-methylpropane sulfonic acid (AMPS: Sigma-Aldrich Japan K.K.), 0.15 g (3.72 mmol) of sodium hydroxide, and 0.93 g (5.66 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of diethyl ether, and the resulting precipitate was collected by filtration under suction. After drying under reduced pressure, 52.0 g of random MAU/AMPS copolymer (99/1) was obtained (yield: 69.2%). The weight average molecular weight was 56000.

Example 3-6

11-Methacrylamidoundecanoic Acid (MAU)/2-acrylamido-2-methylpropanesulfonic Acid (AMPS) Copolymer (99/1)

In 223.30 g of methanol were dissolved 74.23 g (275.63 mmol) of 11-methacrylamidoundecanoic acid (MAU), 0.77 g (3.72 mmol) of 2-acrylamido-2-methylpropanesulfonic acid (AMPS: Sigma-Aldrich Japan K.K.), 0.15 g (3.72 mmol) of sodium hydroxide, and 1.55 g (9.44 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 52.3 g of random MAU/AMPS copolymer (99/1) was obtained (yield: 69.6%). The weight average molecular weight was 36000.

Example 3-7

11-Methacrylamidoundecanoic Acid (MAU)/2-acrylamido-2-methylpropanesulfonic Acid (AMPS) Copolymer (99/1)

In 236.75 g of methanol were dissolved 74.23 g (275.63 mmol) of 11-methacrylamidoundecanoic acid (MAU), 0.77 g (3.72 mmol) of 2-acrylamido-2-methylpropanesulfonic acid (AMPS: Sigma-Aldrich Japan K.K.), 015 g (3.72 mmol) of sodium hydroxide, and 3.10 g (18.88 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 60.1 g of random MAU/AMPS copolymer (99/1) was obtained (yield: 80.0%). The weight average molecular weight was 21000.

Example 3-8

11-Methacrylamidoundecanoic Acid (MAU)/2-acrylamido-2-methylpropanesulfonic Acid (AMPS) Copolymer (90/10)

In 59.4 g of methanol were dissolved 18.42 g (68.41 mmol) of 11-methacrylamidoundecanoic acid (MAU), 1.58 g (7.60 mmol) of 2-acrylamido-2-methylpropanesulfonic acid (AMPS: Sigma-Aldrich Japan K.K.), 0.31 g (7.60 mmol) of sodium hydroxide, and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 17.8 g of random MAU/AMPS copolymer (90/10) was obtained (yield: 87.9%). The weight average molecular weight was 92000.

Example 3-9

11-Methacrylamidoundecanoic Acid (MAU)/2-acrylamido-2-methylpropanesulfonic Acid (AMPS) Copolymer (99/1)

A polymerization inhibitor comprised in MAU was removed by dissolving 11-methacrylamidoundecanoic acid (MAU) in chloroform and passing the solution through an inhibitor remover disposable column (Aldrich Chemical). In 59.91 g of methanol were dissolved 19.85 g (73.69 mmol) of MAU without the polymerization inhibitor, 0.15 g (0.74 mmol) of 2-acrylamido-2-methylpropanesulfonic acid (AMPS: Sigma-Aldrich Japan K.K.), 0.03 g (0.74 mmol) of sodium hydroxide, and 0.06 g (0.37 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 17.33 g of random MAU/AMPS copolymer (99/1) was obtained (yield: 86.6%). The weight average molecular weight was 740000.

Example 3-10

11-Methacrylamidoundecanoic Acid (MAU)/Potassium 3-methacryloxypropanesulfonate Copolymer (90/10)

In 59.69 g of methanol were dissolved 18.15 g (67.41 mmol) of 11-methacrylamidoundecanoic acid (MAU), 1.85 g (7.49 mmol) of potassium 3-methacryloxypropanesulfonate (Tokyo Chemical industry Co.), and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 18.47 g of random MAU/potassium 3-methacryloxypropanesulfonate copolymer (90/10) was obtained (yield: 92.4%). The weight average molecular weight was 240000.

Example 3-11

12-Methacrylamidododecanoic Acid (MAD)/2-acrylamido-2-methylpropanesulfonic Acid (AMPS) Copolymer (99/1)

In 60.0 g of methanol were dissolved 19.85 g (70.14 mmol) of 12-methacrylamidododecanoic acid (MAD), 0.15 g (0.72 mmol) of 2-acrylamido-2-methylpropanesulfonic acid (AMPS: Sigma-Aldrich Japan K.K.), 0.028 g (0.70 mmol) of sodium hydroxide, and 0.29 g (1.77 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of diethyl ether, and the resulting precipitate was collected by filtration under suction. After drying under reduced pressure, 13.5 g of random MAD/AMPS copolymer (99/1) was obtained (yield: 67.5%). The weight average molecular weight was 49000.

Example 3-12

12-Methacrylamidododecanoic Acid (MAD)/2-acrylamido-2-methylpropanesulfonic Acid (AMPS) Copolymer (90/10)

In 60.0 g of methanol were dissolved 18.50 g (65.37 mmol) of 12-methacrylamidododecanoic acid (MAD), 1.50 g (7.24 mmol) of 2-acrylamido-2-methylpropanesulfonic acid (AMPS: Sigma-Aldrich Japan K.K.), 0.29 g (7.25 mmol) of sodium hydroxide, and 0.30 g (1.83 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of diethyl ether, and the resulting precipitate was collected by filtration under suction. After drying under reduced pressure, 15.2 g of random MAD/AMPS copolymer (90/10) was obtained (yield: 75.1%). The weight average molecular weight was 50000.

Example 3-13

12-Methacrylamidododecanoic Acid (MAD)/2-acrylamido-2-methylpropanesulfonic Acid (AMPS) Copolymer (80/20)

In 60.0 g of methanol were dissolved 16.90 g (59.72 mmol) of 12-methacrylamidododecanoic acid (MAD), 3.10 g (14.96 mmol) of 2-acrylamido-2-methylpropanesulfonic acid (AMPS: Sigma-Aldrich Japan K.K.), 0.60 g (1.50 mmol) of sodium hydroxide, and 0.31 g (1.89 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 16.1 g of random MAD/AMPS copolymer (80/20) was obtained (yield: 78.6%). The weight average molecular weight was 95000.

Example 3-14

12-Methacrylamidododecanoic Acid (MAD)/2-acrylamido-2-methylpropanesulfonic Acid (AMPS) Copolymer (70/30)

In 60.0 g of methanol were dissolved 15.22 g (53.78 mmol) of 12-methacrylamidododecanoic acid (MAD), 4.78 g (23.06 mmol) of 2-acrylamido-2-methylpropanesulfonic acid (AMPS: Sigma-Aldrich Japan K.K.), 0.92 g (23.0 mmol) of sodium hydroxide, and 0.32 g (1.95 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 19.0 g of random MAD/AMPS copolymer (70/30) was obtained (yield: 91.6%). The weight average molecular weight was 108000.

Example 3-15

12-Methacrylamidododecanoic Acid (MAD)/2-acrylamido-2-methylpropanesulfonic Acid (AMPS) Copolymer (60/40)

In 60.0 g of methanol were dissolved 13.44 g (47.49 mmol) of 12-methacrylamidododecanoic acid (MAD), 6.56 g (31.65 mmol) of 2-acrylamido-2-methylpropanesulfonic acid (AMPS: Sigma-Aldrich Japan K.K.), 1.27 g (31.75 mmol) of sodium hydroxide, and 0.32 g (1.95 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 20.05 g of random MAD/AMPS copolymer (60/40) was obtained (yield: 95.4%). The weight average molecular weight was 129000.

Example 3-16

12-Methacrylamidododecanoic Acid (MAD)/2-acrylamide-2-methylpropanesulfonic Acid (AMPS) Copolymer (50/50)

In 60.0 g of methanol were dissolved 11.55 g (40.81 mmol) of 12-methacrylamidododecanoic acid (MAD), 8.45 g (40.77 mmol) of 2-acrylamido-2-methylpropanesulfonic acid (AMPS: Sigma-Aldrich Japan K.K.), 1.63 g (40.75 mmol) of sodium hydroxide, and 0.33 g (1.97 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 20.95 g of random MAD/AMPS copolymer (50/50) was obtained (yield: 98.4%). The weight average molecular weight was 176000.

Example 3-17

11-Methacrylamidoundecanoic Acid (MAU)/2-ethylhexyl Acrylate Copolymer (90/10)

In 59.69 g of methanol were dissolved 18.59 g (69.02 mmol) of 11-methacrylamidoundecanoic acid (MAU), 1.41 g (7.67 mmol) of 2-ethylhexyl acrylate (Sigma-Aldrich Japan K.K.), and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, yellow candy-like material was obtained. To this was added 80 g of methanol, and the material was dissolved. The obtained solution was dropwise added into a large excess of ethyl acetate, and the resulting precipitate was collected by filtration under suction. After drying under reduced pressure, 13.01 g of random MAU/2-ethylhexyl acrylate copolymer (90/10) was obtained (yield: 65.0%). The weight average molecular weight was 560000.

Example 3-18

11-Methacrylamidoundecanoic Acid (MAU)/2,2,2-trifluoroethyl acrylate Copolymer (90/10)

In 59.68 g of methanol were dissolved 18.80 g (69.82 mmol) of 11-methacrylamidoundecanoic acid (MAU), 1.20 g (7.76 mmol) of 2,2,2-trifluoroethyl acrylate (Tokyo Chemical industry Co.), and 0.32 g (1.95 mmol) of azoloisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of ethyl acetate, and the resulting precipitate was collected by filtration under suction. After drying under reduced pressure, 9.02 g of random MAU/2,2,2-trifluoroethyl acrylate copolymer (90/10) was obtained (yield: 45.1%). The weight average molecular weight was 35000.

Example 3-19

11-Methacrylamidoundecanoic Acid (MAU)/2,2,3,3-tetrafluoropropyl Methacrylate Copolymer (90/10)

In 59.69 g of methanol were dissolved 18.47 g (68.60 mmol) of 11-methacrylamidoundecanoic acid (MAU), 1.53 g (7.62 mmol) of 2,2,3,3-tetrafluoropropyl methacrylate (Tokyo Chemical industry Co.), and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the reaction solution was dropwise added into a large excess of diethyl ether, and the resulting precipitate was collected by filtration under suction. After drying under reduced pressure, 16.15 g of random MAU/2,2,3,3-tetrafluoropropyl methacrylate copolymer (90/10) was obtained (yield: 80.8%). The weight average molecular weight was 220000.

Example 3-20

11-Methacrylamidoundecanoic Acid (MAU)/2-(N,N-dimethylamino)ethyl Acrylate Copolymer (90/10)

In 59.68 g of methanol were dissolved 18.88 g (70.12 mmol) of 11-methacrylamidoundecanoic acid (MAU), 1.12 g (7.79 mmol) of 2-(N,N-dimethylamino)ethyl acrylate (Tokyo Chemical industry Co.), and 0.32 g (1.95 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the solution was concentrated to dryness under reduced pressure, and the solid was dissolved in 60 g of dimethylformamide. The obtained solution was dropwise added into a large excess of diethyl ether, and the resulting precipitate was collected by filtration under suction. After drying under reduced pressure, 5.22 g of random MAU/2-(N,N-dimethylamino)ethyl acrylate copolymer (90/10) was obtained (yield: 26.1%). The weight average molecular weight was 130000.

Example 3-21

11-Methacrylamidoundecanoic Acid (MAU)/2-dimethylaminoethyl Methacrylate Copolymer (90/10)

In 59.68 g of methanol were dissolved 18.78 g (69.74 mmol) of 11-methacrylamidoundecanoic acid (MAU), 1.22 g (7.75 mmol) of 2-dimethylaminoethyl methacrylate (Tokyo Chemical industry Co.), and 0.32 g (1.95 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the solution was concentrated to dryness under reduced pressure, and the solid was dissolved in 60 g of dimethylformamide. The obtained solution was dropwise added into a large excess of diethyl ether, and the resulting precipitate was collected by filtration under suction. After drying under reduced pressure, 7.78 g of random MAU/2-dimethylaminoethyl methacrylate copolymer (90/10) was obtained (yield: 38.9%). The weight average molecular weight was 250000.

Example 3-22

12-Methacrylamidododecanoic Acid (MAD)/N-hydroxyethylacrylamide (HEAA) Copolymer (90/10)

In 60.0 g of methanol were dissolved 19.14 g (67.63 mmol) of 12-methacrylamidododecanoic acid (MAD), 0.86 g (7.51 mmol) of N-hydroxyethylacrylamide (HEAA: Kohjin Co., Ltd.), and 0.33 g (1.97 mmol) of azobisisobutyronitrile (Nacalai Tesque, Inc.). Before use, azobisisobutyronitrile was recrystallized from methanol in the usual way. The solution was deaerated by bubbling argon for 60 minutes. The container was covered with a septum, and the polymerization was conducted by heating at 60° C. for 20 hours. After the completion of the polymerization reaction, the reaction solution was dropwise added into a large excess of diethyl ether, and the resulting precipitate was collected by filtration under suction. After drying under reduced pressure, 16.90 g of MAD/HEAA copolymer (90/10) was obtained (yield: 84.5%).

Example 3-23

11-Methacrylamidoundecanoic Acid (MAU)/N,N-dimethylaminoethyl Acrylate Methyl Chloride Copolymer (90/10)

In 59.69 g of methanol were dissolved 18.52 g (68.77 mmol) of 11-methacrylamidoundecanoic acid (MAU), 1.48 g (7.64 mmol) of N,N-dimethylaminoethyl acrylate methyl chloride (Kohjin Co., Ltd.), and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the obtained solution was dropwise added into a large excess of acetone, and the resulting precipitate was collected by filtration under suction. After drying under reduced pressure, 9.43 g of random MAU/N,N-dimethylaminoethyl acrylate methyl chloride copolymer (90/10) was obtained (yield: 47.2%). The weight average molecular weight was 68000.

Example 3-24

11-Methacrylamidoundecanoic Acid (MAU)/N,N-dimethylaminopropylacrylamide Methyl Chloride Copolymer (90/10)

In 59.69 g of methanol were dissolved 18.43 g (68.43 mmol) of 11-methacrylamidoundecanoic acid (MAU), 1.57 g (7.60 mmol) of N,N-dimethylaminopropylacrylamide methyl chloride (Kohjin Co., Ltd.), and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the obtained solution was dropwise added into a large excess of acetone, and the resulting precipitate was collected by filtration under suction. After drying under reduced pressure, 9.60 g of random MAU/N,N-dimethylaminopropylacrylamide methyl chloride copolymer (90/10) was obtained (yield: 48.0%). The weight average molecular weight was 42000.

Example 3-25

11-Methacrylamidoundecanoic Acid (MAU)/Methoxypolyethylene Glycol Monomethacrylate Copolymer (90/10)

In 59.70 g of methanol were dissolved 17.96 g (66.67 mmol) of 11-methacrylamidoundecanoic acid (MAU), 2.04 g (7.41 mmol) of methoxypolyethylene glycol monomethacrylate (Blenmer PME-200: Nippon Oil & Fats Co.), and 0.30 g (1.83 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the obtained solution was dropwise added into a large excess of ethyl acetate, and the resulting precipitate was collected by filtration under suction. After drying under reduced pressure, 9.69 g of random MAU/methoxypolyethylene glycol monomethacrylate copolymer (90/10) was obtained (yield: 48.5%). The weight average molecular weight was 110000.

Example 3-26

11-methacrylamidoundecanoic Acid (MAU)/Methoxypolyethylene Glycol Monomethacrylate Copolymer (99/1)

In 59.70 g of methanol were dissolved 19.80 g (73.50 mmol) of 11-methacrylamidoundecanoic acid (MAU), 0.20 g (0.74 mmol) of methoxypolyethylene glycol monomethacrylate (Blenmer PME-200: Nippon Oil & Fats Co.), and 0.30 g (1.83 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the obtained solution was dropwise added into a large excess of ethyl acetate, and the resulting precipitate was collected by filtration under suction. After drying under reduced pressure, 10.28 g of random MAU/methoxypolyethylene glycol monomethacrylate copolymer (99/1) was obtained (yield: 51.4%). The weight average molecular weight was 34000.

Example 3-27

11-Methacrylamidoundecanoic Acid (MAU)/methacryloxy-modified silicone copolymer (90/10)

In a mixed solution of 30 g of methanol and 30 g of chloroform were dissolved 14.16 g (52.57 mmol) of 11-methacrylamidoundecanoic acid (MAU), 5.84 g (5.84 mmol) of methacryloxy-modified silicone (FM-0711: Chisso Corporation), and 0.24 g (1.46 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, the solution was concentrated to dryness under reduced pressure, and the solid was dissolved in 100 g of tetrahydrofuran. The obtained solution was dropwise added into a large excess of n-hexane, and the resulting precipitate was collected by filtration under suction. After drying under reduced pressure, 12.15 g of random MAU/methacryloxy-modified silicone copolymer (90/10) was obtained (yield: 60.8%). The weight average molecular weight was 53000.

Example 3-28

11-Methacrylamidoundecanoic Acid (MAU)/2-methacryloxyethyl Phosphoric Acid Copolymer (90/10)

In a mixed solvent of 75 g of methanol and 25 g of ion-exchanged water were dissolved 18.40 g (68.32 mmol) of 11-methacrylamidoundecanoic acid (MAU), 1.60 g (7.59 mmol) of 2-methacryloxyethyl phosphoric acid (Phosmer-M: Uni-Chemical Co.), 0.30 g (7.59 mmol) of sodium hydroxide, and 0.31 g (1.89 mmol) of azobisisobutyronitrile (Nacalai Tesque, Inc.). The solution was deaerated by bubbling nitrogen for 60 minutes. The container was covered with a septum, and the polymerization was conducted by heating at 60° C. for 20 hours. After the completion of the polymerization reaction, a gelatinous product was obtained. This product was dried under reduced pressure, and 6.0 g of the dried material was added to 200 g of methanol. After sufficient stirring, insoluble material was removed by filtration. The obtained solution was dropwise added into a large excess of ethyl acetate, and the resulting precipitate was collected by filtration under suction. After drying under reduced pressure, 2.01 g of random MAU/2-methacryloxyethyl phosphoric acid copolymer (90/10) was obtained. The weight average molecular weight was 190000.

Example 4

In the following section are shown formulation examples of cosmetics in which the powders treated with various surface-treating agents described in the above examples are blended.

| Example 4-1 Powder solid foundation | mass % |
|---|---|
| Dimethylpolysiloxane | 5 |
| Isostearic acid | 0.5 |
| Diisostearyl malate | 1 |
| Glyceryl tri2-ethylhexanoate | 3 |
| Sorbitan sesquiisostearate | 1 |
| Spherical PMMA coated mica | 4 |
| Fineparticle zinc oxide | 1 |
| Fineparticle titanium oxide | 3 |
| Synthetic phlogopite | 1 |
| Metallic soap treated talc | Balance |
| Spheric silica | 3 |
| Red iron oxide coated titanated mica | 1 |
| Anhydrous silicic acid coated mica | 6 |
| DL-alpha-tocopherol acetate | 0.1 |
| D-sigma-tocopherol | 0.1 |
| Ethylparaben | q.s. |
| Methyl bis(trimethylsiloxy)silylisopentyl trimethoxycinnamate | 0.1 |
| 2-Ethylhexyl p-methoxycinnamate | 3 |
| Spheric polyalkylacrylate powder | 2 |
| Polyalkylacrylate powder including liquid paraffin | 4 |
| Treated talc with Example 3-13 *1 | 20 |
| Treated sericite with Example 3-13 *2 | 15 |
| Treated titania with Example 3-13 *1 | 10 |
| Treated yellow iron oxide (coloring material) with Example 3-13 *1 | 4.2 |
| Treated red iron oxide (coloring material) with Example 3-13 *1 | 0.7 |
| Treated black iron oxide (coloring material) with Example 3-13 *1 | 0.1 |

*1 Powder:Polymer = 80:20(mass %)
*2 Powder:Polymer = 75:25(mass %)

| Example 4-2 Powder solid foundation | mass % |
|---|---|
| Alpha-olefine oligomer | 3 |
| Petrolatum | 2 |
| Synthetic hydrocarbon wax powder | 2 |
| Dimethylpolysiloxane | 3 |
| Isostearic acid | 1 |
| Glyceryl tri2-ethylhexanoate | 3 |
| Sorbitan sesquiisostearate | 1 |
| Glycerol modified silicone resin coated talc | 5 |

| Example 4-2 Powder solid foundation | mass % |
|---|---|
| Treated synthetic phlogopite with Example 3-18 *3 | 27 |
| Treated titania with Example 3-18 *4 | 5 |
| Boron nitride | 1 |
| Treated sericite with Example 3-18 *3 | 20 |
| Treated talc with Example 3-18 *3 | Balance |
| Treated mica with Example 3-18 *4 | 5 |
| Treated barium sulfate with Example 3-18 *4 | 1 |
| Red iron oxide coated titanated mica | 0.1 |
| DL-alpha-tocopherol acetate | 0.1 |
| D-delta-tocopherol | 0.1 |
| Parahydroxybenzoic acid ester | q.s |
| Red iron oxide coated titanated mica | q.s |
| Treated yellow iron oxide with Example 3-18 *3 | q.s |
| Treated black iron oxide with Example 3-18 *3 | q.s |
| Nylon powder | 2 |
| Silicic anhydride | 2 |
| Spheric polyalkylacrylate powder | 6 |

*3 Powder:Polymer = 80:20(mass %)
*4 Powder:Polymer = 75:25(mass %)

| Example 4-3 Powder solid foundation | mass % |
|---|---|
| Synthetic hydrocarbon wax particle | 2 |
| Dimethylpolysiloxane | 6 |
| Purified lanolin | 5 |
| Glyceryl tri2-ethyl hexanoate | 2 |
| Sorbitan sesquiisostearate | 0.5 |
| Treated needle-shape fineparticle titania with Example 3-12 *5 | 5 |
| Treated fineparticle zinc oxide with Example 3-12 *5 | 1 |
| Treated iron oxide/titania sintered material with Example 3-12 *6 | 7 |
| Treated barium sulfate with Example 3-12 *5 | 8 |
| Treated sericite carcined material with Example 3-12 *6 | Balance |
| Titanium-deoxided titanated mica pearl pigments | 2 |
| Treated synthetic phlogopite with Example 3-18 *6 | 5 |
| Treated talc with Example 3-12 *6 | 2 |
| Spheric silica | 3 |
| Treated mica with Example 3-12 *6 | 15 |
| Stearyl glycyrrhetate | 0.1 |
| Ascorbyl dipalmitate | 0.1 |
| DL-alpha-tocopherol acetate | 0.1 |
| D-delta-tocopherol | 0.1 |
| Parahydroxybenzoic acid ester | q.s. |
| Ethylhexyl methoxycinnamate | 3 |
| Treated red iron oxide with Example 3-12 *6 | 1 |
| Treated yellow iron oxide in Example 3-12 *6 | 1 |
| Treated black iron oxide in Example 3-12 *6 | 1 |
| Spheric polyalkyl acrylate | 3 |
| Perfume | q.s. |

*5 Powder:Polymer = 85:15(mass %)
*6 Powder:Polymer = 75:25(mass %)

| Example 4-4 Powder solid foundation | mass % |
|---|---|
| Alpha-olefine oligomer | 10 |
| Microcrystalline wax | 0.5 |
| Ceresin | 5 |
| Dimethylpolysiloxane | 15 |
| Methylphenyl polysiloxane | 10 |
| Macadamia nuts oil | 0.1 |
| Carnauba wax | 0.1 |
| Glyceryl tri2-ethylhexanoate | 7 |
| Cetyl 2-ethylhexanoate | 10 |
| Sorbitan sesquiisostearate | 1.5 |
| Treated mica with Example 3-1 | 0.5 |
| Aluminum stearate | 1 |
| Cross-linked silicone powder (Trefil E-506) | 8 |
| N-Lauroyl-L-lisine | 0.1 |
| D-delta-tocopherol | q.s. |

| Example 4-4 Powder solid foundation | mass % |
|---|---|
| Treated red iron oxide with Example 3-2 + behenyl alcohol | q.s. |
| Treated yellow iron oxide with Example 3-2 + behenyl alcohol | q.s. |
| Calcium alginate powder | 1 |
| Nylon powder | Balance |
| Treated spherical anhydrous silicic acid with Example 3-2 + behenyl alcohol | 1 |
| Treated titania with Example 3-2 + behenyl alcohol | 1 |

*Powder:Polymer:Behenyl alcohol = 75:20:5(mass %)

| Example 4-5 Powder solid foundation | mass % |
|---|---|
| Microcrystalline wax | 5 |
| Dimethylpolysiloxane | 10 |
| Decamethylcyclopentasiloxane | 30 |
| Polyoxyethylene/methylpolysiloxane copolymer | 2 |
| Dipropylene glycol | 3 |
| Palmitic acid | 0.5 |
| Sorbitan sesquiisostearate | 1 |
| Treated yellow iron oxide with Example 3-9 + isostearic acid *7 | 3 |
| Treated red iron oxide Example 3-9 + isostearic acid *7 | 1 |
| Treated black iron oxide with Example 3-9 + isostearic acid *7 | q.s. |
| Treated anhydrous silicic acid with Example 3-9 + isostearic acid *8 | 2 |
| Treated titania with Example 3-9 + isostearic acid *7 | 15 |
| Treated sericite with Example 3-9 + isostearic acid *8 | 10 |
| Treated titania/red iron oxide coated mica with Example 3-9 + isostearic acid *8 | 3 |
| Cross-linked silicone powder (Trefil E-506) | 3 |
| N-Lauroyl-L-lisine | 0.1 |
| Tocopheryl acetate | 0.1 |
| Delta-tocopherol | 0.1 |
| Parahydroxybenzoic acid ester | q.s. |
| Melilot extract | 2 |
| Purified water | Balance |

*7 Powder:Polymer:Isostearic acid = 75:20:5(mass %)
*8 Powder:Polymer:Isostearic acid = 75:15:10(mass %)

| Example 4-6 Powder solid foundation | mass % |
|---|---|
| Microcrystalline Wax | 1 |
| Dimethylpolysiloxane | 15 |
| Decamethylcyclopentasiloxane | 2 |
| 1,3-Butylene glycol | 6 |
| Candelilla wax | 3 |
| Isostearic acid | 1 |
| Ethylene glycol fatty acid ester | 0.1 |
| Octyldodecyl lanolate | 0.5 |
| 2-alkyl-N-carboxymethyl-N-hydroxyethylimidazolinium betaine | 4 |
| Treated pigment class titania with Example 3-21 | 7.5 |
| Treated barium sulfate with Example 3-21 | 5 |
| Treated fineparticle titania with Example 3-21 | 7 |
| Treated talc with Example 3-21 | 3 |
| Treated silicic anhydrid with Example 3-21 | 4 |
| Cross-linked silicone powder (Trefil E-506) | 0.1 |
| Sodium metaphosphate | 0.1 |
| Hydroxypropyl cyclodextrin | 0.1 |
| DL-alpha-tocopherol acetate | 0.1 |
| *Hamamelis* extract | 0.1 |
| Peony root extract | 0.1 |
| Sodium chondroitin sulphate | 0.1 |
| Sodium hyaluronate | 0.1 |
| Parahydroxybenzoic acid ester | q.s. |
| Treated red iron oxide with Example 3-21 | q.s. |
| Treated yellow iron oxide with Example 3-21 | q.s. |
| Treated black iron oxide with Example 3-21 | q.s. |
| Xanthan gum | 0.2 |

| Example 4-6 Powder solid foundation | mass % |
|---|---|
| Carboxymethyl cellulose sodium | 0.2 |
| Melilot extract | 2 |
| Purified water | Balance |

*Powder:Polymer = 75:25(mass %)

| Example 4-7 Powder solid foundation | mass % |
|---|---|
| Ceresin | 5 |
| Dimethylpolysiloxane | 10 |
| Decamethylcyclopentasiloxane | 10 |
| Dodecamethylcyclohexasiloxane | 20 |
| Carnauba wax | 0.5 |
| Candelilla wax | 0.5 |
| Glyceryl tri2-ethylhexanoate | Balance |
| Sorbitan sesquiisostearate | 1.5 |
| Treated titania with Example 3-3 | 8 |
| Treated kaolin with Example 3-3 | 10 |
| Treated mica with Example 3-3 | 12 |
| Titanated mica/polyalkyl acrylatecomposite powder | 1 |
| Polyalkylacrylate coated titanated mica | 1 |
| Treated titania MT-014TV with Example 3-3 | 5 |
| Treated black iron oxide coated titanated mica with Example 3-3 | 0.5 |
| Tocopheryl acetate | 0.1 |
| Delta-tocopherol | 0.1 |
| Treated red iron oxide with Example 3-3 | q.s. |
| Treated yellow iron oxide with Example 3-3 | q.s. |
| Treated iron blue with zinc oxide | q.s. |
| Treated black iron oxide with Example 3-3 | q.s. |
| Perfume | q.s. |

*Powder:Polymer = 75:25(mass %)

| Example 4-8 Powder solid foundation | mass % |
|---|---|
| Dimethylpolysiloxane | 15 |
| Decamethylcyclopentasiloxane | 20 |
| Polyoxyethylene/methylpolysiloxane copolymer | 5 |
| High moleculer weight amino modified silicone | 0.1 |
| Glycerin | 5 |
| 1,3-Butylene glycol | 10 |
| Palmitic acid | 0.5 |
| Cholesteryl macadamiate | 0.1 |
| Distearyldimethylammonium chloride | 0.2 |
| Treated yellow iron oxide with Example 3-19 | 2 |
| Treated red iron oxide with Example 3-19 | 1 |
| Treated black iron oxide with Example 3-19 | 0.3 |
| Treated titania with Example 3-19 | 10 |
| Treated talc with Example 3-19 | 1.5 |
| Treated spindle-shape titania with Example 3-19 | 3 |
| L-sodium glutamate | 0.5 |
| DL-alpha-tocopherol acetate | 0.1 |
| Parahydroxybenzoic acid ester | q.s. |
| Methyl bis(trimethylsiloxy)sirylisopentil trimethoxycinnamate | 0.1 |
| Dimethyldistearylammonium hectorite | 1.5 |
| Spheric nylon powder | 1 |
| Purified water | Balance |
| Perfume | q.s. |

*Powder:Polymer = 75:25(mass %)

| Example 4-9 Powder solid foundation | mass % |
|---|---|
| Dimethylpolysiloxane | 3 |
| Decamethylcyclopentasiloxane | 15 |
| Polyoxyethylene/methylpolysiloxane copolymer | 3 |

| Example 4-9 Powder solid foundation | mass % |
|---|---|
| Glycerin | 3 |
| 1,3-Butylene glycol | 5 |
| Palmitic acid | 0.5 |
| Distearyldimethylammonium chloride | 0.2 |
| Glycerol modified silicone resin coated sericite | 0.5 |
| Treated yellow iron oxide coated titanated mica with Example 3-11 *9 | 0.5 |
| Treated titania with Example 3-11 *9 | 2 |
| Treated iron oxide/titania sintered material (PK) with Example 3-11 *10 | 12 |
| Treated talc with Example 3-11 *9 | 10 |
| Treated titania coated sericite with Example 3-11 *10 | 0.5 |
| Boron nitride | 0.5 |
| Fineparticle titanium oxide | 0.5 |
| Treated red iron oxide coated titanated mica with Example 3-11 *10 | 0.5 |
| Phytosterol | 0.1 |
| L-sodium glutamate | 1.5 |
| Ascorbyl dipalmitate | 0.1 |
| DL-alpha-tocopherol acetate | 0.1 |
| Acetylated sodium hyaluronate | 0.1 |
| Parahydroxybenzoic acid ester | q.s. |
| Phenoxyethanol | q.s. |
| Red iron oxide coated titanated mica | 0.5 |
| Treated yellow iron oxide with Example 3-11 *9 | 2 |
| Treated black iron oxide with Example 3-11 *9 | 0.2 |
| Spheric nylon powder | 1 |
| Purified water | Balance |
| Perfume | q.s. |

*9 Powder:Polymer = 80:20(mass %)
*10 Powder:Polymer = 75:25(mass %)

| Example 4-10 Powder solid foundation | mass % |
|---|---|
| Behenyl alcohol | 0.5 |
| Dipropylene glycol | 6 |
| Stearic acid | 1 |
| Glyceryl monostearate | 1 |
| Potassium hydroxide | 0.2 |
| Triethanolamine | 0.8 |
| DL-alpha-tocopherol acetate | 0.1 |
| Parahydroxybenzoic acid ester | q.s. |
| Treated yellow iron oxide with Example 3-4 | 1 |
| Alpha-olefine oligomer | 3 |
| Dimethylpolysiloxane (6 mPa · s) | 2 |
| Dimethylpolysiloxane (100 mPa · s) | 5 |
| Batylalcohol | 0.5 |
| Isostearic acid | 1 |
| Behenic acid | 0.5 |
| Cetyl 2-ethylhexanoate | 10 |
| Polyoxyethylene glycerin monostearate | 1 |
| Treated titania with Example 3-4 | 3 |
| Titanated mica/polyalkyl acrylate composite powder | 0.5 |
| Treated fineparticle titania with Example 3-4 | 10 |
| Polyalkylacrylate coated titanated mica | 0.5 |
| Treated black iron oxide coated titanated mica in Example 3-4 | 0.5 |
| Treated silicic anhydride with Example 3-4 | 6 |
| 2-Ethylhexyl p-methoxycinnamate | 2 |
| Treated red iron oxide with Example 3-4 | q.s. |
| Treated iron blue with Example 3-4 | q.s. |
| Treated black iron oxide with Example 3-4 | q.s. |
| Legal coloring pigment | q.s. |
| Xanthan gum | 0.1 |
| Bentonite | 1 |
| Sodium carboxymethylcellulose | 0.1 |
| Purified water | Balance |
| Perfume | q.s. |

*Powder:Polymer = 85:15(mass %)

| Example 4-11 Powder solid foundation | mass % |
|---|---|
| Dodecamethylcyclohexasiloxane | 15 |
| Decamethylcyclopentasiloxane | Balance |
| 3-Tris(trimethylsiloxy) silylpropyl carbamoyl pullulan | 3 |
| Ethanol | 10 |
| Isostearic acid | 0.5 |
| Treated zinc oxide with Example 3-11 | 0.5 |
| Treated titania with Example 3-12 | 10 |
| Treated talc with Example 3-12 | 7 |
| Treated fineparticle titania with Example 3-12 | 5 |
| Cross-linked silicone powder | 1 |
| Spheric silicic anhydride | 2 |
| Magnesium ascorbyl phosphate | 0.2 |
| DL-alpha-tocopherol acetate | 0.1 |
| D-delta-tocopherol | 0.1 |
| Glutathione | 0.1 |
| *Sophora* Extract | 0.1 |
| 2-Ethylhexyl p-methoxycinnamate | 5 |
| Treated red iron oxide with Example 3-11 | q.s. |
| Treated yellow iron oxide with Example 3-11 | q.s. |
| Treated black iron oxide with Example 3-11 | q.s. |
| Perfume | q.s. |

*Powder:Polymer (execution example 3-11) = 85:15(mass %)
Powder:Polymer (execution example 3-12) = 90:10(mass %)

| Example 4-12 Powder solid foundation | mass % |
|---|---|
| Decamethylcyclopentasiloxane | 10 |
| Dodecamethylcyclohexasiloxane | 20 |
| Trimethylsiloxysilicate | 1 |
| Poly (oxyethylene/oxypropylene) methylpolysiloxane copolymer | 3 |
| Ethanol | 10 |
| Isostearic acid | 0.5 |
| Treated titania with Example 3-16 | 10 |
| Treated fineparticle zinc oxide with Example 3-16 | 5 |
| Dextrin palmitate coated talc | 5 |
| Treated needle-shape fineparticle titania with Example 3-16 | 1 |
| Treated spherical anhydrous silicic acid with Example 3-16 | 5 |
| Anhydrous silicic acid coated mica | q.s. |
| Sodium citrate | q.s. |
| N-Lauroyl-L-lisine | 0.5 |
| DL-alpha-tocopherol acetate | 0.1 |
| D-delta-tocopherol | 0.1 |
| *Sophora* extract | 1 |
| Treated red iron oxide with Example 3-16 | q.s. |
| Treated yellow iron oxide with Example 3-16 | q.s. |
| Treated black iron oxide with Example 3-16 | q.s. |
| Melilot extract | 2 |
| Purified water | Balance |

*Powder:Polymer = 80:20(mass %)

| Example 4-13 Powder solid foundation | mass % |
|---|---|
| Ethyl alcohol | 2 |
| Glycerin | 2 |
| 1,3-Butylene glycol | 6 |
| Treated titania (30 μm) with Example 3-20 | 4 |
| Treated titania (ultrafineparticle: 20 nm) with Example 3-20 | 2 |
| Treated zinc oxide with Example 3-20 | 2 |
| Treated plate-shape barium sulfate with Example 3-20 | 5 |
| Treated talc with Example 3-20 | 1 |
| Treated kaolin with Example 3-20 | 2 |
| Treated mica with Example 3-20 | 0.5 |
| Treated spheric silica in Example 3-20 | 0.5 |
| Salt | 0.3 |
| L-Arginine hydrochloride | 0.1 |
| Creeping thyme extract | 0.1 |
| Hamamelis | 0.1 |
| *Phellodendron* extract | 0.1 |
| Peppermint extract BG | 0.1 |
| Phenoxyethanol | 0.5 |
| Red iron oxide | 0.5 |
| Ocre | 1 |
| Treated iron oxide black with Example 3-20 | 0.7 |
| Magnesium aluminometasilicate | 0.1 |
| Ion-exchanged water | Balance |

*Powder:Polymer = 95:5(mass %)

| Example 4-14 Powder solid foundation | mass % |
|---|---|
| Ethanol | 2.0 |
| Glycerin | 10.0 |
| 1,3-Butylene glycol | 15.0 |
| Silica coated titania | 8.0 |
| Treated synthetic phlogopite with Example 3-10 | 3.0 |
| Spheric silicic anhydride | 5.0 |
| Treated red iron oxide coated titanated mica (color rendering pearl G) with Example 3-10 | 2.0 |
| Sodium chloride | 0.3 |
| Hydroxypropyl beta-cyclodextrin | 0.1 |
| *Mukurossi* Extract | 0.1 |
| Sweet tea extract | 0.1 |
| Lily extract | 0.1 |
| Red iron oxide | 0.1 |
| Gellan gum | 0.1 |
| Porous spheric cellulose | 0.1 |
| Lavender extract | 0.1 |
| Purified water | Balance |

*Powder:Polymer = 95:5(mass %)

| | Example 4-15 POW oil-in-water emulsified milky foundation | mass % |
|---|---|---|
| (1) | Treated titania with Example 3-13 | 9.0 |
| (2) | Treated ultrafine particle titania(40 nm) with Example 3-13 | 5.0 |
| (3) | Treated iron oxide(red) with Example 3-13 | 0.5 |
| (4) | Treated iron oxide(yellow) with Example 3-13 | 1.5 |
| (5) | Treated iron oxide(black) with Example 3-13 | 0.2 |
| (6) | Polyoxyalkylene modified organopolysiloxane | 0.5 |
| (7) | Decamethylpentacycrosiloxane | 5.0 |
| (8) | Octyl p-methoxycinnamate | 5.0 |
| (9) | Acrylic silicone | 4.0 |
| (10) | PEG-100 hydrogenated castor oil | 2.0 |
| (11) | Dynamite glycerin | 6.0 |
| (12) | Xanthan Gum | 0.1 |
| (13) | Carboxymethylcellulose | 0.3 |

-continued

| | Example 4-15 POW oil-in-water emulsified milky foundation | mass % |
|---|---|---|
| (14) | Sodium acryloyldimethyltaurate/hydroxy ethyl acrylate copolymer (content: 35-40 mass %) (SIMULGEL NSTM: Seppic) | 1.5 |
| (15) | Ethanol | 3.0 |
| (16) | Ion-exchanged water | Balance |

* Powder:Polymer = 80:20(mass %)

(Manufacturing method) (1)-(9) were mixed and dispersed, then this was added into an aqueous phase dissolving (10)-(16) with homomixer.

| Example 4-16 O/W type mascara | mass % |
|---|---|
| Microcrystalline wax | 6 |
| Methylpolysiloxane emulsion | q.s. |
| Isopropanol | 3 |
| Batylalcohol | 1 |
| Dipropylene glycol | 5 |
| Isostearic acid | 3 |
| Stearic acid | 1 |
| Di(phytostearyl/2-octyldodecyl) N-lauroyl-L-glutamate | 0.1 |
| Sorbitan monostearate | 1 |
| Polyoxyethylene (20EO) solbitan monostearate | 1 |
| Sucrose fatty acid ester | 15 |
| Isobutylene/sodium maleate copolymer solution | 0.1 |
| Titanated mica | 1 |
| Potassium hydroxide | 0.5 |
| Sodium hydrogen carbonate | 0.1 |
| DL-alpha-tocopherol acetate | 0.1 |
| Parahydroxybenzoic acid ester | q.s. |
| Sodium dehydroacetate | q.s. |
| Phenoxyethanol | q.s. |
| Treated black iron oxide (coloring material) with Example 3-13 | 10 |
| Seaweed extract | 0.1 |
| Magnesium aluminum silicate | 0.1 |
| Polyalkylacrylate emulsion | 5 |
| Polyvinyl alcohol | 0.5 |
| Polyvinyl acetate emulsion | 7 |
| Purified water | Balance |
| Silicic anhydride | 0.5 |
| Treated titania with Example 3-13 | 0.1 |

| Example 4-17 O/W type mascara | mass % |
|---|---|
| Light isoparaffin | 6 |
| Dimethylpolysiloxane | 1 |
| Decamethylcyclopentasiloxane | 5 |
| Trimethylsiloxy silicate | 5 |
| Methylpolysiloxane emulsion | q.s. |
| Isopropanol | 3 |
| 1,3-Butylene glycol | 6 |
| Polyoxyethylene hydrogenated castor oil | 1 |
| Sucrose fatty acid ester | 0.6 |
| Diglyceryl diisostearate | 1 |
| Sodium hydrogen carbonate | 0.01 |
| DL-alpha-tocopherol acetate | 0.1 |
| Acetylated sodium hyaluronnate | 0.1 |
| Parahydroxybenzoic acid ester | q.s. |
| Phenoxyethanol | 0.3 |
| Treated black iron oxide with Example 3-13 | 8 |
| Bentonite | 1 |
| Dimethyldistearylammonium hectorite | 4 |
| Polyvinyl alcohol | 4 |
| Alkylacrylate copolymer emulsion | 12 |
| Polyvinyl acetate emulsion | 12 |
| Nylon fiber (1-2 mm) | 6 |
| Purified water | Balance |
| Silicic anhydride | 0.5 |
| Treated titania with Example 3-13 | 1 |
| Perfume | q.s. |

| Example 4-18 O/W type eyeliner | mass % |
|---|---|
| Liquid paraffin | 5 |
| Methylpolysiloxane emulsion | q.s. |
| Glycerin | 3 |
| 1,3-Butylene glycol | 6 |
| Polyoxyethylene (20EO) solbitan monolaurate | 2 |
| Isobutylene/sodium maleate copolymer | 1 |
| Treated titania with Example 3-13 | q.s. |
| Plate-shape barium sulfate | q.s. |
| Treated kaolin with Example 3-13 | 8 |
| Black iron oxide coated titanated mica (pearl ingredient) | 3 |
| Treated black iron oxide with Example 3-13 | 9 |
| DL-alpha-tocopherol acetate | 0.1 |
| Parahydroxybenzoic acid ester | q.s. |
| Bentonite | 1 |
| Sodium carboxymethylcellulose | 2 |
| Alkyl acrylate copolymer emulsion | 7 |
| Purified water | Balance |

| Example 4-19 Pencil-type eyeliner | mass % |
|---|---|
| Liquid paraffin | Balance |
| Microcrystalline wax | 20 |
| Macadamia nuts oil | 0.1 |
| Candelilla wax | 2 |
| Sorbitan sesquiisostearate | 1 |
| Treated titania with Example 3-13 | 1 |
| Treated mica with Example 3-13 | 5 |
| Treated titanated mica with Example 3-13 | 15 |
| Treated synthetic micas with Example 3-13 | 0.1 |
| Treated iron blue coated titanated mica with Example 3-13 | 2 |
| Treated red iron oxide coated titanated mica with Example 3-13 | 2 |
| Treated mica with Example 3-13 | 10 |
| DL-alpha-tocopherol acetate | 0.02 |
| D-delta-Tocopherol | 0.02 |
| Glyceryl di(p-methoxy cinnamate) mono(2-ethylhexanoate) | 0.1 |
| Treated zinc oxide with iron blue | 2 |
| Iron blue | 5 |
| Heavy liquid isoparaffin | 1 |
| Polyalkyl acrylate powder | 2 |
| Cross-linked silicone powder | 5 |

| Example 4-20 Solid type eyeliner | mass % |
|---|---|
| Petrolatum | 3 |
| Hardened oil | 30 |
| Japan wax | 10 |

| Example 4-20 Solid type eyeliner | mass % |
|---|---|
| Stearic acid | 12 |
| Trimethylolpropane triethyloctanoate | 5 |
| Treated titania with Example 3-13 | 2 |
| Treated titanated mica with Example 3-13 | 10 |
| Treated red iron oxide with Example 3-13 | 2 |
| Treated yellow iron oxide with Example 3-13 | 0.5 |
| Treated iron blue with Example 3-13 | 5 |
| Treated black iron oxide with Example 3-13 | 1 |
| Treated mica with Example 3-13 | Balance |

| Example 4-21 Pencil-type eyebrow | mass % |
|---|---|
| Hardened oil | 10 |
| Macadamia nuts oil | 0.1 |
| Soybean oil | 0.1 |
| Japan wax | 10 |
| Behenic acid | Balance |
| Diisostearyl malate | 1 |
| Glyceryl tri2-ethylhexanoate | 2 |
| Sucrose fatty acid ester | 5 |
| Treated titania with Example 3-13 | 4 |
| Treated mica with Example 3-13 | 2 |
| Delta-tocopherol | 0.05 |
| Treated red iron oxide with Example 3-13 | 8 |
| Treated yellow iron oxide with Example 3-13 | 13 |
| Treated black iron oxide with Example 3-13 | 14 |
| Adsorption purified lanolin | 5 |
| Spheric nylon powder | 3 |

| Example 4-22 Pencil-type eyebrow | mass % |
|---|---|
| Decamethylcyclopentasiloxane | 10 |
| Polyoxyethylene/methylpolysiloxane copolymer | 0.5 |
| Methylphenylpolysiloxane | q.s. |
| Behenyl alcohol | 14 |
| Macadamia nuts oil | 0.1 |
| Carnauba wax | 2 |
| Candelilla wax | 13 |
| Sorbitan sesquiisostearate | 0.5 |
| Treated titania with Example 3-13 | 1 |
| Treated red iron oxide coated titanated mica with Example 3-13 | 0.1 |
| Treated sericite with Example 3-13 | Balance |
| Silicic anhydride | 0.5 |
| Mica | 6 |
| Delta-tocopherol | 0.05 |
| Treated red iron oxide with Example 3-13 | 2 |
| Treated yellow iron oxide with Example 3-13 | 3 |
| Treated black iron oxide with Example 3-13 | 8 |
| Trimethylsiloxysilicate | 8 |
| Polyethylene wax | 2 |

| Example 4-23 Pencil-type lipliner | mass % |
|---|---|
| Herdened oil | 20 |
| Macadamia nuts oil | 2 |
| Japan wax | 6 |
| Behenic acid | 10 |
| Glyceryl tri2-ethylhexanoate | Balance |
| Sucrose fatty acid ester | 5 |
| Treated titania with Example 3-13 | 10 |
| Treated mica with Example 3-13 | 10 |
| D-delta-tocopherol | 0.04 |
| Treated red iron oxide with Example 3-13 | 13 |
| Treated yellow iron oxide with Example 3-13 | 5 |
| Treated black iron oxide with Example 3-13 | 2 |
| Sorbitan sesquiisostearate | 1 |

| Example 4-24 Pencil-type lipliner | mass % |
|---|---|
| Polyethylene wax | 8 |
| Ceresin | 4 |
| Macadamia nuts oil | 0.1 |
| Liquid lanolin | 0.1 |
| Carnauba wax | 1 |
| Candelilla wax | 10 |
| Phytosteryl hydroxystearate | 0.1 |
| Glyceryl triisostearate | 15 |
| Diisostearyl malate | 0.1 |
| Glyceryl diisostearate | Balance |
| Trimethylolpropane trioctanoate | 5 |
| Glyceryl tri2-ethylhexanoate | 13 |
| Treated yellow iron oxide with Example 3-13 | 5 |
| Treated red iron oxide with Example 3-13 | 7 |
| Treated black iron oxide with Example 3-13 | 0.5 |
| Treated titania with Example 3-13 | 0.1 |
| Barium sulfate | 1.5 |
| Silicic anhydride | 0.5 |
| Tocopherol acetate | 0.02 |
| Delta-tocopherol | 0.02 |
| 4-tert-butyl-4'-methoxydibenzoylmethane | 0.1 |
| Glyceryl di(p-methoxy cinnamate) mono(2-ethylhexanoate) | 0.1 |
| Pigment | 1 |
| Heavy liquid isoparaffin | 15 |

| Example 4-25 Stick-type lip rouge | mass % |
|---|---|
| Ceresin | 6 |
| Decamethylcyclopentasiloxane | Balance |
| Polyoxyethylene/methylpolysiloxane copolymer (MW = 6000) | 5 |
| Non-aqueous dispersion (Dispersion of alkyl acrylate/tris(trimethylsiloxy)silylpropyl methacrylate in decamethylcycropentasiloxane) | 30 |
| Dimethylsiloxane/diphenylsiloxane/methyl(Perfluoro-alkyl)siloxane | 20 |
| Methylphenyl polysiloxane | 5 |
| Stearoxymethyl polysiloxane | 2 |
| Candelilla wax | 4 |
| Silylated silicic anhydride | 1 |
| Treated silicone coated pigments (titania, iron oxide red etc.)with Example 3-13 | 7 |
| Treated red iron oxide coated titanated mica with Example 3-13 | 5 |
| Treated mica with Example 3-13 | 1 |
| Dye | q.s. |
| Silicic anhydride | 2 |
| Treated titania with Example 3-13 | 3 |
| Poly(oxyethylene/oxypropylene)/methylpolysiloxane copolymer (MW = 50000) | 2 |
| Perfume | q.s. |

| Example 4-26 Emulsion-type lip rouge | mass % |
|---|---|
| Microcrystalline wax | 3 |
| Ceresin | 2 |
| Polyoxyethylene/methylpolysiloxane copolymer | 0.5 |
| Methylphenyl polysiloxane | Balance |
| Glycerin | 0.5 |
| Xylitol | 0.1 |

| Example 4-26 Emulsion-type lip rouge | mass % |
|---|---|
| Liquid lanolin | 2 |
| Squalane | 1 |
| Glycerine triisostearate | 1 |
| Cholesteryl macadamiate | 2 |
| Gryceryl tri(2-ethylhexanoate) | 15 |
| Glyceryl tri(hydrogenated rosinate/isostearate) | 10 |
| Treated silicon resin coated titania with Example 3-13 | 1 |
| Treated calmine coated mica titanium with Example 3-13 | 2 |
| Treated titanated mica with Example 3-13 | 5 |
| Dye | q.s. |
| Citric acid | 0.1 |
| Potassium hydroxide | 0.05 |
| Hydroxypropyl cyclodextrin | 0.3 |
| Pantothenyl ethyl ether | 0.05 |
| Arginine hydrochloride | 0.01 |
| DL-alpha-tocopherol acetate | 0.05 |
| Sodium hyaluronnate | 0.05 |
| 2-Ethylhexyl p-methoxycinnamate | 5 |
| Spheric cellulose powdere | 2 |
| Heavy liquid isoparaffin | 20 |
| Purified water | 0.5 |
| Perfume | q.s. |

| Example 4-27 Middle plate-type lip rouge | mass % |
|---|---|
| Liquid paraffin | 11 |
| Carnauba wax | 2 |
| Glyceryl tri2-ethylhexanoate | Balance |
| Sorbitan sesquioleate | 1 |
| treated titania with Example 3-13 | 5 |
| Treated titanated mica with Example 3-13 | 12 |
| Treated mica with Example 3-13 | 17 |
| Treated iron blue with Example 3-13 | 5 |
| Treated black iron oxide in Example 3-13 | 1 |

| Example 4-28 Liquid tip-type lip rouge | mass % |
|---|---|
| Liquid paraffin | Balance |
| Ceresin | 5 |
| Heavy liquid isoparaffin | 30 |
| Methylphenyl polysiloxane | 5 |
| Liquid lanolin | 3 |
| Diisostearyl malate | 15 |
| Polyethylene terephtalate/polymethyl metacrylate laminated film powder | 3 |
| Treated silicone coated pigments with Example 3-13 (Bengala, iron oxide and titania, etc.) | 3 |
| Treated red iron oxide coated titanated mica with Example 3-13 | 2 |
| Polyoxyethylene/methylpolysiloxane copolymer | 0.5 |
| 1,3-Butylene glycol | 3 |
| Hydrogenated lecithin | 0.1 |
| Calcium chloride | 0.1 |
| Sodium hyaluronnate | 0.02 |
| Parabene | q.s. |
| Laponite | 1.5 |
| Purified water | 1 |

| Example 4-29 Powder solid eye shadow | mass % |
|---|---|
| Liquid paraffin | 0.5 |
| Petrolatum | 1 |
| Methylphenyl polysiloxane | 2 |
| Sorbitan sesquiisostearate | 1 |
| Treated titania with Example 3-13 | 0.1 |
| Treated mica with Example 3-13 | 10 |
| Treated synthetic mica with Example 3-13 | 2 |
| Treated sericite with Example 3-13 | 30 |
| Treated talc with Example 3-13 | Balance |
| Zinc myristate | 2 |
| D-delta-Tocopherol | 0.02 |
| Parahydroxybenzoic acid ester | q.s. |
| Treated yellow iron oxide with Example 3-13 | 2 |
| Treated black iron oxide with Example 3-13 | 20 |
| Pigment | q.s. |
| Diisostearyl malate | 3 |

| Example 4-30 Oily stick-type eye shadow | mass % |
|---|---|
| Paraffin | 11 |
| Carnauba wax | 1.5 |
| Glyceryl tri2-ethylhexanoate | balance |
| Sorbitan sesquioleate | 2 |
| Treated titania with Example 3-13 | 3 |
| Treated titanated mica with Example 3-13 | 15 |
| Treated mica with Example 3-13 | 20 |
| Treated iron blue with Example 3-13 | 2 |
| Treated black iron oxide with Example 3-13 | 5 |
| Perfume | q.s. |

| Example 4-31 Oily middle plate-type eye shadow | mass % |
|---|---|
| Alpha-olefine oligomer | 2 |
| Microcrystalline wax | 1.5 |
| Ceresin | 6 |
| Dimethylpolysiloxane | 5 |
| Methylphenyl polysiloxane | 5 |
| Carnauba wax | 2 |
| Gryceryl tri2-ethylhexanoate | 20 |
| Cetyl 2-ethylhexanoate | Balance |
| Sorbitan sesquiisostearate | 1 |
| Treated titania with Example 3-13 | 3 |
| Treated boron nitride with Example 3-13 | 5 |
| Treated titanated mica with Example 3-13 | 10 |
| Treated sericite with Example 3-13 | 8 |
| Cross-linked silicone powder | 5 |
| DL-alpha-tocopherol acetate | 0.02 |
| D-delta-tocopherol | 0.02 |
| Treated red iron oxide with Example 3-13 | 0.1 |
| Treated yellow iron oxide with Example 3-13 | 0.2 |
| Polyalkyl acrylate powder | 15 |
| Perfume | q.s. |
| 12-Hydroxystearic acid | 3 |

| Example 4-32 W/O type sunscreen | mass % |
|---|---|
| Decamethylcyclopentasiloxane | 20 |
| Trimethylsiloxysilicate | 1 |
| Polyoxyethylene/methylpolysiloxane copolymer | 2 |
| Dipropylene glycol | 4 |
| Squalane | 5 |
| Treated silicone coated microprticle titania (20 nm) with Example 3-13 | 10 |
| Treated talc(hydophobing material) with Example 3-13 | 6 |
| Parabene | q.s. |
| Phenoxyethanol | q.s. |
| Trisodium edetate | 0.02 |
| 4-t-butyl-4'-methoxydibenzoylmethane | 0.1 |
| 2-Ethylhexyl p-methoxycinnamate | 7 |
| Glyceryl di(p-methoxycinnamate) mono(2-ethylhexanoate) | 0.5 |
| Spheric polyethylene powder | 5 |

| Example 4-32 W/O type sunscreen | mass % |
|---|---|
| Dimethyldistearylammonium hectorite | 1 |
| Purified water | Balance |
| Perfume | q.s. |

| Example 4-33 W/O type sunscreen | mass % |
|---|---|
| Dimethylpolysiloxane | 5 |
| Decamethylcyclopentasiloxane | 20 |
| Trimethylsiloxysilicate | 3 |
| Polyoxyethylene/methylpolysiloxane copolymer | 3 |
| Dipropylene glycol | 3 |
| Cetyl 2-ethylhexanoate | 1 |
| Treated silicone coating fineparticle zinc oxide (60 nm) with Example 3-13 | 10 |
| Treated talc with Example 3-13 | 1 |
| Treated Silicone coated fineparticle titania(40 nm) with Example 3-137 | |
| Parabene | q.s. |
| Phenoxyethanol | q.s. |
| Trisodium edetate | 0.2 |
| Dimethyldistearylammonium hectorite | 1 |
| Polymethyl methacrylate copolymer spherical powder | 3 |
| Purified water | Balance |
| Perfume | q.s. |

| Example 4-34 W/O type sunscreen | mass % |
|---|---|
| Decamethylcyclopentasiloxane | 20 |
| Ethanol | 5 |
| Isostearyl alcohol | 2 |
| Dipropylene glycol | 3 |
| Isostearic acid | 2 |
| Glyceryl tri2-ethylhexanoate | 5 |
| Cetyl 2-ethylhexanoate | 2 |
| Treated dextrin fatty acid ester coated fineparticle titanium oxide(40 nm) with Example 3-13 | 2 |
| Sodium chloride | 2 |
| Trisodium edetate | q.s. |
| Yubinal T-150 (BASF) | 1 |
| 4-t-butyl-4'-methoxydibenzoylmethane | 1 |
| Ethylhexyl methoxycinnamate | 7.5 |
| Sodium carboxymethylcellulose | 0.5 |
| Ethyl cellulose | 1 |
| Spheric acrylic resin powder | 5 |
| Purified water | Balance |
| Perfume | q.s. |

| Example 4-35 O/W type sunscreen | mass % |
|---|---|
| Dimethylpolysiloxane | 5 |
| Decamethylcyclopentasiloxane | 25 |
| Trimethylsiloxysilicate | 5 |
| Polyoxyethylene/methylpolysiloxane copolymer | 2 |
| Dipropylene glycol | 5 |
| Treated fineparticle zinc oxide (Hydrophobic treated material 60 nm) with Example 3-13 | 15 |
| Parabene | q.s. |
| Phenoxyethanol | q.s. |
| Trisodium edetate | q.s. |
| 2-Ethylhexyl p-methoxycinnamate | 7.5 |
| Dimethyldistearylammonium hectorite | 0.5 |
| Spheric polyalkyl acrylate powder | 5 |
| Purified water | Balance |
| Perfume | q.s. |

| Example 4-36 O/W type sunscreen | mass % |
|---|---|
| Dipropylene glycol | 5 |
| Stearic acid | 1 |
| Palmitic acid | 1 |
| Glyceryl tri2-ethylhexanoate | 3 |
| Cetyl 2-ethylhexanoate | 2 |
| Polyoxyethylene glyceryl isostearate | 1 |
| Glyceryl monostearate | 1 |
| Polyoxyethylene glyceryl monostearate | 1 |
| Treated fineparticle titania (30 nm) with Example 3-13 | 2 |
| Sodium hexametaphosphate | 0.1 |
| Phenoxyethanol | q.s. |
| Trisodium edetate | q.s. |
| 4-t-butyl-4'-methoxydibenzoylmethane | 1 |
| 2-Ethylhexyl p-methoxycinnamate | 7 |
| Bentonite | 1 |
| Eicosene/vinylpyrrolidone copolymer | 2 |
| Purified water | q.s. |
| Perfume | q.s. |

| Example 4-37 W/O type sunscreen | mass % |
|---|---|
| Dimethylpolysiloxane | 5 |
| Decamethylcyclopentasiloxane | 25 |
| Trimethylsiloxysilicate | 5 |
| Polyoxyethylene/methylpolysiloxane copolymer | 2 |
| Dipropylene glycol | 5 |
| Treated dextrin palmitate coated fineparticle zinc oxide(60 nm) with Example 3-13 | 15 |
| Dipotassium glycyrrhizinate | 0.02 |
| Glutathione | 1 |
| Thiotaurine | 0.05 |
| Sophora Extract | 1 |
| Parabene | q.s. |
| Phenoxyethanol | q.s. |
| Trisodium edetate | q.s. |
| 2-Ethylhexyl p-methoxycinnamate | 7.5 |
| Dimethyldistearylammonium hectorite | 0.5 |
| Spheric polyalkyl acrylate powder | 5 |
| Butylethylpropanediol | 0.5 |
| Purified water | Balance |
| Perfume | q.s. |

| Example 4-37 W/O type protector | mass % |
|---|---|
| Dimethylpolysiloxane | 2 |
| Decamethylcyclopentasiloxane | 25 |
| Dodecamethylcyclohexasiloxane | 10 |
| Polyoxyethylene/methylpolysiloxane copolymer | 1.5 |
| Trimethylsiloxysilicate | 1 |
| 1,3-Butylene glycol | 5 |
| Squalane | 0.5 |
| Talc | 5 |
| Dipotassium glycyrrhizinate | 0.1 |
| Tocopheryl acetate | 0.1 |
| Trisodium edetate | 0.05 |
| 4-t-butyl-4'-methoxydibenzoylmethane | 1 |
| 2-Ethylhexyl p-methoxycinnamate | 5 |
| Glyceryl di(p-methoxycinnamate) mono(2-ethylhexanoate) | 1 |
| Treated silicone coated fineparticle titania(40 nm) with Example 3-13 | 4 |
| Dimethyldistearylammonium hectorite | 0.5 |
| Spheric polyethylene powder | 3 |
| Phenoxyethanol | q.s. |
| Purified water | Balance |
| Perfume | q.s. |

What is claimed is:

1. A surface-treated powder comprising:
powder particles having a surface; and
a polymer including at least 70 mole % of a monomer (A) represented by the general formula (1) described below as a constituent monomer:

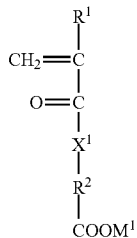
(1)

wherein $R^1$ represents a hydrogen atom or an alkyl group having 1 to 3 carbon atoms, $R^2$ represents an alkylene group having 4 to 22 carbon atoms, $X^1$ represents an —NH— group or an oxygen atom, and $M^1$ represents a hydrogen atom or a monovalent inorganic or organic cation, wherein the polymer is coated on the surface of the powder particles.

2. The surface-treated powder of claim 1, wherein the polymer further comprises a monomer (B) represented by any one of general formulas (2) to (7):

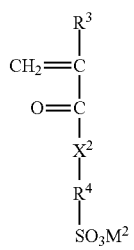
(2)

wherein $R^3$ represents a hydrogen atom or an alkyl group having 1 to 3 carbon atoms, $R^4$ represents an alkylene group having 1 to 4 carbon atoms, $X^2$ represents an —NH— group or an oxygen atom, and $M^2$ represents a hydrogen atom or a monovalent inorganic or organic cation;

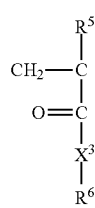
(3)

wherein $R^5$ represents a hydrogen atom or an alkyl group having 1 to 3 carbon atoms, $R^6$ represents an alkyl group having 1 to 10 carbon atoms, a fluoroalkyl group, an aminoalkyl group, or a hydroxyalkyl group, and $X^3$ represents an —NH— group or an oxygen atom;

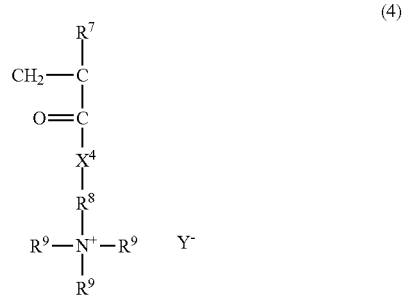
(4)

wherein $R^7$ represents a hydrogen atom or an alkyl group having 1 to 3 carbon atoms, $R^8$ represents an alkylene group having 1 to 4 carbon atoms, $R^9$'s may be the same or different and each represents a hydrogen atom or an alkyl group having 1 to 4 carbon atoms, $X^4$ represents an —NH— group or an oxygen atom, and $Y^-$ represents a monovalent organic or inorganic anion;

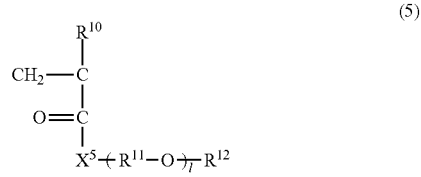
(5)

wherein $R^{10}$ represents a hydrogen atom or an alkyl group having 1 to 3 carbon atoms, $R^{11}$ represents an alkylene group having 1 to 4 carbon atoms, $R^{12}$ represents a hydrogen atom or an alkyl group having 1 to 4 carbon atoms, $X^5$ represents an —NH— group or an oxygen atom, and l stands for an integer of 1 to 100;

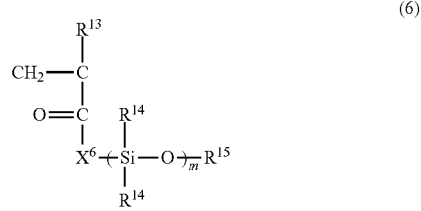
(6)

wherein $R^{13}$ represents a hydrogen atom or an alkyl group having 1 to 3 carbon atoms, the constituents $R^{14}$ may be the same or different and each represents a hydrogen atom or an alkyl group having 1 to 4 carbon atoms, $R^{15}$ represents a hydrogen atom or an alkyl group having 1 to 4 carbon atoms, $X^6$ represents an —NH— group or an oxygen atom, and m stands for an integer of 1 to 100; and,

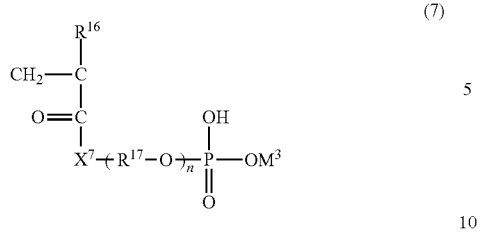

(7)

wherein $R^{16}$ represents a hydrogen atom or an alkyl group having 1 to 3 carbon atoms, $R^{17}$ represents an alkylene group having 1 to 4 carbon atoms, $X^7$ represents an —NH— group or an oxygen atom, $M^3$ represents a hydrogen atom or a monovalent inorganic or organic cation, and n stands for an integer of 1 to 100.

3. The surface-treated powder of claim 2, wherein the mole ratio (A):(B) of monomer (A) to monomer (B) is from 70:30 to 99.9:0.1.

4. The surface-treated powder of claim 1, wherein the mass ratio of the polymer to the powder is from 3:97 to 40:60.

5. A cosmetic comprising the surface-treated powder of claim 1.

6. A cosmetic comprising the surface-treated powder of claim 2.

7. A cosmetic comprising the surface-treated powder of claim 3.

8. A cosmetic comprising the surface-treated powder of claim 4.

* * * * *